(12) United States Patent
DeLuca et al.

(10) Patent No.: US 7,538,098 B2
(45) Date of Patent: May 26, 2009

(54) 19-NOR-VITAMIN D ANALOGS WITH 1,2 OR 3,2 HETEROCYCLIC RING

(75) Inventors: Hector F. DeLuca, Deerfield, WI (US); Rafal R. Sicinski, Warsaw (PL); Agnieszka Glebocka, Madison, WI (US); Lori A. Plum, Arena, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 46 days.

(21) Appl. No.: 11/697,424

(22) Filed: Apr. 6, 2007

(65) Prior Publication Data

US 2007/0238712 A1 Oct. 11, 2007

Related U.S. Application Data

(60) Provisional application No. 60/791,227, filed on Apr. 6, 2006.

(51) Int. Cl.
*A61K 31/59* (2006.01)
*C07D 401/00* (2006.01)
(52) U.S. Cl. .................... 514/167; 552/653
(58) Field of Classification Search ........... 514/167; 552/653
See application file for complete search history.

(56) References Cited

U.S. PATENT DOCUMENTS

| | | | |
|---|---|---|---|
| 4,188,345 A | 2/1980 | DeLuca et al. |
| 4,411,833 A | 10/1983 | DeLuca et al. |
| 4,666,634 A | 5/1987 | Miyamoto et al. |
| 4,970,203 A | 11/1990 | DeLuca et al. |
| 5,086,191 A | 2/1992 | DeLuca et al. |
| 5,536,713 A | 7/1996 | DeLuca et al. |
| 5,585,369 A | 12/1996 | DeLuca et al. |
| 5,843,928 A | 12/1998 | DeLuca et al. |
| 5,880,114 A | 3/1999 | DeLuca et al. |
| 5,936,133 A | 8/1999 | DeLuca et al. |
| 5,945,410 A | 8/1999 | DeLuca et al. |
| 6,127,559 A | 10/2000 | DeLuca et al. |

(Continued)

FOREIGN PATENT DOCUMENTS

| WO | WO 98/41501 | 9/1988 |
|---|---|---|
| WO | WO 02/058707 | 8/2002 |

OTHER PUBLICATIONS

Baggiolini et al., "Stereocontrolled Total Synthesis of 1α,25-Dihydroxycholecalciferol and 1α,25-Dihydroxyergocalciferol," Journal of Organic Chemistry, 51, pp. 3098-3108, (1986).

(Continued)

*Primary Examiner*—Sabiha N. Qazi
(74) *Attorney, Agent, or Firm*—Andrus, Sceales, Starke & Sawall, LLP

(57) ABSTRACT

19-nor-vitamin D analogs having an additional heterocyclic ring connecting the 3β-oxygen and carbon-2 or the 1α-oxygen and carbon-2 of the A-ring of the analog, and pharmaceutical uses therefore, are described. These compounds exhibit significant activity in mobilization of bone, making them therapeutic agents for the treatment or prophylaxis of osteoporosis, osteomalacia, osteopenia, renal osteodystrophy and hypoparathyroidism.

81 Claims, 6 Drawing Sheets

U.S. PATENT DOCUMENTS

| | | | |
|---|---|---|---|
| 6,277,837 B1 | 8/2001 | DeLuca et al. | |
| 6,291,444 B1 | 9/2001 | DeLuca et al. | |
| 6,306,844 B1 | 10/2001 | DeLuca et al. | |
| 6,382,071 B1 | 5/2002 | Bertani et al. | |
| 6,537,981 B2 | 3/2003 | DeLuca et al. | |
| 6,566,352 B1 | 5/2003 | DeLuca et al. | |
| 6,579,861 B2 | 6/2003 | DeLuca et al. | |
| 6,627,622 B2 * | 9/2003 | DeLuca et al. | 514/167 |
| 6,844,330 B2 | 1/2005 | DeLuca et al. | |
| 6,844,331 B2 | 1/2005 | DeLuca et al. | |
| 6,844,332 B2 | 1/2005 | DeLuca et al. | |
| 6,844,457 B2 | 1/2005 | DeLuca et al. | |
| 6,846,811 B2 | 1/2005 | DeLuca et al. | |
| 6,887,860 B2 * | 5/2005 | DeLuca et al. | 514/167 |
| 7,053,075 B2 | 5/2006 | DeLuca et al. | |
| 2003/0158157 A1 | 8/2003 | DeLuca et al. | |
| 2004/0229851 A1 | 11/2004 | DeLuca et al. | |
| 2005/0119242 A1 | 6/2005 | DeLuca et al. | |
| 2007/0191316 A1 | 8/2007 | DeLuca et al. | |
| 2007/0191317 A1 | 8/2007 | DeLuca et al. | |

OTHER PUBLICATIONS

Collins et al, "Normal Functional Characteristics of Cultured Human Promyelocytic Leukemia Cells (HL-60) After Inducation of Differentiation by Dimethylsulfoxide," The Journal of Experimental Medicine, vol. 149, pp. 969-974, (1979).

Corey et al, "Computer-Assisted Synthetic Analysis. A Rapid Computer Method for the Semiquantitative Assignment of Conformation of Six-Membered Ring Systems. 1. Derivation of a Preliminary Conformational Description of the Six-Membered Ring," The Journal of Organic Chemistry, vol. 45, No. 5, pp. 757-764, (1980).

Daniewski et al, "A Novel Silylcopper Catalyst for the Reductive Bromination of Hajos Dione. Improved Preparation of a CD Synthon for the Synthesis of Vitamin D," Journal of Organic Chemistry, vol. 66, No. 2, pp. 626-628, (2001).

Fall et al, "Vitamin D Heterocyclic Analogues. Part 1: A Stereoselective Route to CD Systems with Pyrazole Rings in their Side Chains," Tetrahedron Letters 43, pp. 1433-1436, (2002).

Glebocka et al, "New Derivative of 1α,25-Dihydroxy-19-Norvitamin $D_3$ with 3'-Alkoxypropylidene Moiety at C-2: Synthesis, Biological Activity and Conformational Analysis," Journal of Steroid Biochemistry & Molecular Biology, vols. 89-90, pp. 25-30, (2004).

Granja et al, "Studies on the Opening of Dioxanone and Acetal Templates and Application to the Synthesis of 1α,25-Dihydroxyvitamin $D_2$," Journal of Organic Chemistry, vol. 58, pp. 124-131, (1993).

Hanessian et al, "Total Synthesis of (—)-Reserpine Using the Chiron Approach," Journal of Organic Chemistry, vol. 62, pp. 465-473, (1997).

Inhoffen et al, "Studies in the Vitamin D Series, XXI: Hydrindane Compounds from Vitamin $D_3$," Chemische Berichte, vol. 90, pp. 664-673, (1957).

Lythgoe et al, "Calciferol and it Relatives. Part22. A Direct Total Synthesis of Vitamin $D_2$ and Vitamin $D_3$," J. Chem. Soc. Perkin Trans. 1, p. 590, (1978).

Lythgoe, "Synthetic Approaches to Vitamin D and its Relatives," Chem. Soc. Rev. 9, p. 449, (1983).

Minicione et al, "Improved Conversion of Vitamin $D_2$ into the Windaus Ketone and its Regioselective Hydroxylation via Organoboranes at $C_{26}$," Synthetic Communications, vol. 19 Nos. 5-6, pp. 723-735, (1989).

Miyamoto et al, "Synthetic Studies of Vitamin D Analogues. XIV. Synthesis and Calcium Regulating Activity of Vitamin $D_3$ Analogues Bearing a Hydroxyalkoxy Group at the 2β-Position," Chem. Pharm. Bull., vol. 41, No. 6, pp. 1111-1113, (1993).

Nishii et al, "The Development of Vitamin $D_3$ Analogues for the Treatment of Osteoporosis," Osteoporosis Int., Suppl. 1, pp. S190-S193, (1993).

Okamura et al, "Vitamin D: Concerning the Relationship Between Molecular Topology and Biological Function," Proc. Nat. Acad. Sci. U.S.A., vol. 71, No. 10, pp. 4194-4197 (1974).

Okano et al, "Regulatory Activities of 2β-(3-Hydroxypropoxy)-1α,25-Dihydroxy-Vitamin $D_3$, a Novel Synthetic Vitamin $D_3$ Derivative, on Calcium Metabolism," Biochemical and Biophysical Research Communications, vol. 163 No. 3, pp. 1444-1449, (1989).

Ono et al, "Efficient Synthesis of 2-Modified 1α,25-Dihydroxy-19-norvitamin $D_3$ with Julia Olefination: High Potency in Induction of Differentiation on HL-60 Cells," Journal of Orgainic Chemistry, vol. 68, pp. 7407-7415, (2003).

Ostrem et al, "24- and 26-homo-1,25-dihydroxyvitamin $D_3$: Preferential activity in inducing differentiation of human leukemia cells HL-60 in vitro," Proc. Natl. Acad. Sci. USA, vol. 84, pp. 2610-2614, (1987).

Perlman et al, "1α,25-Dihydroxy-19-Nor-Vitamin $D_3$. A Novel Vitamin D-Related Compound with Potential Therapeutic Activity," Tetrahedron Letters, vol. 31 No. 13, pp. 1823-1824, (1990).

Perlman et al, "Novel Synthesis of 19-Nor-Vitamin D Compounds," Tetrahedron Letters, vol. 32 No. 52, pp. 7663-7666, (1991).

Peterson et al, "Studies of the Ketone Obtained from the Ozonolysis of Vitamin D. Molecular Mechanics Calculations for It and Related Hydrindanones," Journal of Organic Chemistry, vol. 51 No. 11, pp. 1948-1954 (1986).

Plum et al, "Biologically Active Noncalcemic Analogs of 1α,25-Dihydroxyvitamin D with an Abbreviated Side Chain Containing No Hydroxyl," PNAS, vol. 101 No. 18, pp. 6900-6904, (2004).

Posner et al, "Stereocontrolled Total Synthesis of Calcitriol Derivatives: 1,25-Dihydroxy-2-(4'-hydroxybutyl)vitamin $D_3$ Analogs of an Osteoporosis Drug," Journal of Organic Chemistry, vol. 59 No. 25, pp. 7855-7861, (1994).

Posner et al, "2-Fluoroalkyl A-Ring Analogs of 1,25-Dihydroxyvitamin $D_3$. Stereocontrolled Total Synthesis via Intramolecular and Intermolecular Diets—Alder Cycloadditions. Preliminary Biological Testing," Journal of Organic Chemistry, vol. 60 No. 14, pp. 4617-4628, (1995).

Rochel et al, "The Crystal Structure of the Nuclear Receptor for Vitamin D Bound to Its Natural Ligand," Molecular Cell, vol. 5, pp. 173-179, (2000).

Sardina et al, "Studies on the Synthesis of Side-Chain Hydroxylated Metabolites of Vitamin D. 2. Stereocontrolled Synthesis of 25-Hydroxyvitamin $D_2$," J. Org. Chem., 51, pp. 1264-1269, (1986).

Sicinski et al, "New 1α,25-Dihydroxy-19-Norvitamin $D_3$ Compounds of High Biological Activity: Synthesis and Biological Evaluation of 2-Hydroxymethyl, 2-Methyl, and 2-Methylene Analogues," Journal of Medical Chemistry, 41, pp. 4662-4674, (1998).

Sicinski et al, "New Highly Calcemic 1α,25-Dihydroxy-19-Norvitamin $D_3$ Compounds with Modified Side Chain: 26,27-Dihomo- and 26,27-Dimethylene Analogs in 20S-Series," Steroids, vol. 67, pp. 247-256, (2002).

Sicinski et al, "2-Ethyl and 2-Ethylidene Analogues of 1α,25-Dihydroxy-19-Norvitamin $D_3$: Synthesis, Conformational Analysis, Biological Activities, and Docking to the Modeled rVDR Ligand Binding Domain," Journal of Medical Chemistry, vol. 45, pp. 3366-3380, (2002).

Tocchini-Valentini et al, "Crystal Structures of the Vitamin D Receptor Complexed to Superagonist 20-epi Ligands," Proc. Natl. Acad. Sci. USA, vol. 98 No. 10, pp. 5491-5496, (2001).

Toh et al, "Studies on a Convergent Route to Side-Chain Analogues of Vitamin D: 25-Hydroxy-23-Oxavitamin $D_3$," J. Org. Chem., 48, 1414, (1983).

Windaus et al, "The Constitution of Vitamin $D_2$ Part II," Annalen der Chemie, 524, pp. 295-299, (1936).

Yoshida et al, "Efficient on Convergent Coupling Route for the Short-step Synthesis of Enantiopure 2α- and 2β-Alkylated 1α,25-Dihydroxy-19-norvitamin $D_3$ Analogues," Synlett, No. 8, pp. 1175-1179, (2003).

Sicinski et a, "An Analog of 1α,25-Dihydroxy-19-Norvitamin $D_3$ with the 1α-Hydroxy Group Fixed in the Axial Position Lacks Biological Activity in vitro," Journal of Steroid Biochemistry & Molecular Biology, vol. 103, pp. 293-297, (2007).

PCT International Search Report, PCT/IB2007/003641, dated Jun. 10, 2008.

* cited by examiner

19-NOR-VITAMIN D ANALOGS WITH 1,2 OR 3,2 HETEROCYCLIC RING

CROSS REFERENCE TO RELATED APPLICATION

This application claims priority to and the benefit of U.S. Provisional Application No. 60/791,227, filed Apr. 6, 2006.

BACKGROUND OF THE INVENTION

The natural hormone, 1α,25-dihydroxyvitamin $D_3$ and its analog in ergosterol series, i.e. 1α,25-dihydroxyvitamin $D_2$ are known to be highly potent regulators of calcium homeostasis in animals and humans, and more recently their activity in cellular differentiation has been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies.

In 1990, a new class of vitamin D analogs was discovered, i.e. the so called 19-nor-vitamin D compounds, characterized by the replacement of the ring A exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, with very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Letters 31, 1823 (1990); Perlman et al., Tetrahedron Letters 32, 7663 (1991), and DeLuca et al., U.S. Pat. No. 5,086,191). A few years later, analogs of 1α,25-dihydroxy-19-norvitamin $D_3$ substituted at 2-position with hydroxy or alkoxy groups (DeLuca et al., U.S. Pat. No. 5,536,713) were synthesized. It has been established that they exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the transposition of the ring A exocyclic methylene group from carbon 10 (C-10) to carbon 2 (C-2), i.e. 2-methylene-19-nor-vitamin D compounds have been recently synthesized and tested (Sicinski et al., J. Med. Chem., 41, 4662 (1998); Sicinski et al., Steroids 67, 247 (2002); DeLuca et al., U.S. Pat. Nos. 5,843,928, 5,936,133 and 6,382,071). Molecular mechanics studies, performed on these analogs, showed that a change of ring-A conformation can be expected resulting in the "flattening" of the cyclohexanediol ring. From molecular mechanics calculations and NMR studies their A-ring conformational equilibrium was established to be ca. 6:4 in favor of the conformer that has an equatorial 1α-OH. Introduction of the 2-methylene group into 19-nor-vitamin D carbon skeleton changes the character of its (1α- and 3β-) A-ring hydroxyls; they are both now in the allylic positions, similar to the 1α-hydroxyl group (crucial for biological activity) in the molecule of the natural hormone, 1α,25-$(OH)_2D_3$. It was found that 1α,25-dihydroxy-2-methylene-19-norvitamin D analogs are characterized by significant biological potency, enhanced dramatically in compounds with an "unnatural" (20S)-configuration.

Very recently, 2-ethylidene analogs of 1α,25-dihydroxy-19-norvitamin $D_3$ have been synthesized. It turned out that such modification of the ring A results in significant biological potency of compounds, especially enhanced in the E-geometrical isomers, Sicinski et al., J. Med. Chem., 45, 3366 (2002). Interestingly, it has been established that E-isomers have A-ring conformational equilibrium considerably shifted to one particular chair form, that possessing 1α-hydroxyl in an equatorial orientation. Also, the analogs which are characterized by the presence of substituted propylidene moiety at C-2 have also been synthesized and preliminary biological tests indicated strong and selective (intestinal) calcemic activity of the E-geometrical isomers.

A-ring conformational equilibrium in vitamin D compounds has attracted considerable research interest for more than 30 years. Development of NMR spectroscopy and force field calculation methods made it possible to establish, or even predict, the proportion of equilibrating α- and β-chair A-ring forms. Parallel to these studies another, closely related problem has been discussed in the literature, namely the correlation of A-ring conformation with biological activities of vitamin D compounds. As early as in 1974 it was proposed [Okamura et al., Proc. Natl. Acad. Sci. USA, 71, 4194 (1974)] that equatorial orientation of 1α-hydroxy group (i.e., the β-chair form) is necessary for the calcium regulation ability. Recently, Moras reported the crystal structures of hVDR ligand binding domain (LBD) bound to the natural hormone [Moras et al, Moll. Cell, 5, 173 (2000)] and the ligands with unnatural configuration at C-20, [Moras et al, Proc. Natl. Acad. Sci. USA, 98, 5491 (2001)] and it became clear that vitamin D receptor binds (at least in the crystalline state) to vitamin D analogs having their A-rings in β-chair conformation. It seemed, therefore, interesting to synthesize a vitamin D analog that could only assume the opposite α-chair conformation of its ring A, and as a consequence, possesses 1α-hydroxy group in the axial orientation.

As a continuation of the search for biologically active 2-alkylidene-19-norvitamin D compounds, analogs which are characterized by the presence of an additional ring and "flattening bond" system [Corey et al, J. Org. Chem., 45, 757 (1980)] have also been synthesized and tested. Such 19-norvitamin D compounds seemed interesting targets because structural constrains of their molecules would prevent their ring A from flipping over to the alternative β-chair form, effectively "freezing" the A-ring α-chair conformation.

SUMMARY OF THE INVENTION

The present invention is directed toward 1α,25-dihydroxy and 3β,25-dihydroxy-19-nor-vitamin $D_3$ analogs, their biological activity, and various pharmaceutical uses for these compounds.

A class of 1α-hydroxylated vitamin D compounds not known heretofore are the vitamin D isomers having the A-ring exocyclic methylene moiety at C-10 removed and possessing an additional ring connecting 3β-oxygen and C-2. Also, their geometrical isomers possessing an additional ring connecting 1α-oxygen and C-2 represent the unknown class of 19-norvitamin D compounds. Structurally these novel ana logs are characterized by the general formula I and II shown below:

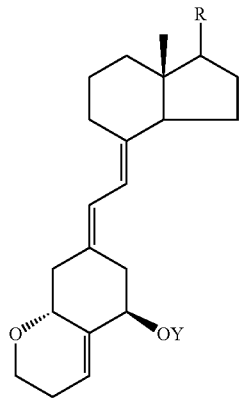

I

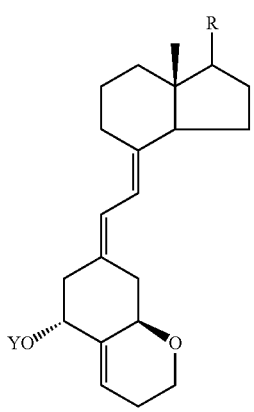

II where Y is selected from the group consisting of hydrogen and a hydroxy-protecting group, and where the group R represents any of the typical side chains known for vitamin D type compounds. Thus, R may be an alkyl, hydrogen, hydroxyalkyl or fluoroalkyl group, or R may represent a side chain of the formula:

where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^5$ and a radical of the structure:

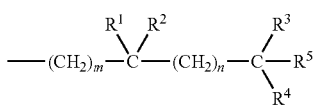

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group ═CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

The wavy line to the carbon 20 indicates that carbon 20 may have either the R or S configuration.

Specific important examples of side chains with natural 20R-configuration are the structures represented by formulas (a), b), (c), (d) and (e) below. i.e. the side chain as it occurs in 25-hydroxyvitamin D$_3$ (a); vitamin D$_3$ (b); 25-hydroxyvitamin D$_2$ (c); vitamin D$_2$ (d); and the C-24 epimer of 25-hydroxyvitamin D$_2$ (e).

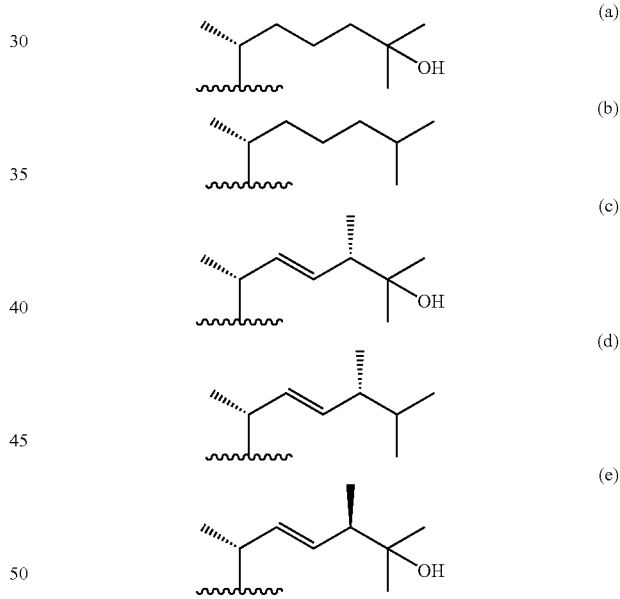

The above compounds of formulae I and II exhibit a desired, and highly advantageous, pattern of biological activity. These compounds are characterized by having significant ability to mobilize calcium from bone, as compared to 1α,25-dihydroxyvitamin D$_3$. Their preferential activity on calcium mobilizing activity allows the in vivo administration of these compounds for the treatment and prophylaxis of metabolic bone diseases. Because of their preferential calcemic activity on bone, these compounds would be preferred therapeutic agents for the treatment and prophylaxis of metabolic bone diseases such as osteoporosis, especially low bone turnover osteoporosis, steroid induced osteoporosis, senile osteoporosis or postmenopausal osteoporosis, as well as osteomalacia, osteopenia, renal osteodystrophy and vitamin D resistant rickets. These analogs having significant bone calcium mobilizing activity while being somewhat active on cell differentiation are also expected to be useful as a therapy to treat hypoparathyroidism since they are effective to raise blood calcium levels.

The compounds of the invention of formula I and II are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I and/or II. Administration of one or more of the compounds or the pharmaceutical compositions to the subject inhibit adipocyte differentiation, inhibits gene transcription, and/or reduces body fat in the animal subject.

One or more of the compounds may be present in a composition to treat or prevent the above-noted diseases and disorders in an amount from about 0.01 µg/gm to about 10 mg/gm of the composition, preferably from about 0.1 µg/gm to about 1 mg/gm of the composition, and may be administered topically, transdermally, orally, rectally, nasally, sublingually, or parenterally in dosages of from about 0.01 µg/day to about 10 mg/day, preferably from about 0.1 µg/day to about 1 mg/day.

BRIEF DESCRIPTION OF THE DRAWINGS

FIG. 1 is a graph illustrating the relative activity of REV-A, REV-B and 1,25$(OH)_2D_3$ to compete for binding with [$^3$H]-1,25-$(OH)_2$-$D_3$ to the full-length recombinant rat vitamin D receptor;

FIG. 2 is a graph illustrating the percent HL-60 cell differentiation as a function of the concentration of REV-A, REV-B and 1,25$(OH)_2D_3$;

FIG. 3 is a graph illustrating the in vitro transcription activity of 1,25$(OH)_2D_3$ as compared to REV-A and REV-B; and FIG. 4 is a bar graph illustrating the bone calcium mobilization activity of 1,25$(OH)_2D_3$ as compared to REV-A and REV-B, and more specifically, it shows the serum calcium change in response to a single, intraperitoneal injection in D-deficient CD-1 mice. Statistical significance (p<0.05) compared to the vehicle group is indicated by an asterisk.

FIG. 5 is a bar graph similar to FIG. 4 illustrating the bone calcium mobilization activity of 1,25$(OH)_2D_3$ as compared to REV-A and REV-B, except FIG. 5 shows the serum calcium change in response to a single, intraperitoneal injection in D-sufficient CD-1 mice given at two different doses for each compound. Statistical significance (p<0.05) compared to the vehicle group is indicated by an asterisk.

FIG. 6 is a bar graph similar to FIGS. 4 and 5 illustrating bone calcium mobilization activity of 1,25$(OH)_2D_3$ as compared to REV-B, except FIG. 6 shows the serum calcium change in response to different routes of administration in D-sufficient CD-1 mice given at different doses for each compound. Statistical significance (p<0.05) compared to the vehicle group is indicated by an asterisk.

DETAILED DESCRIPTION OF THE INVENTION

Figure 1:
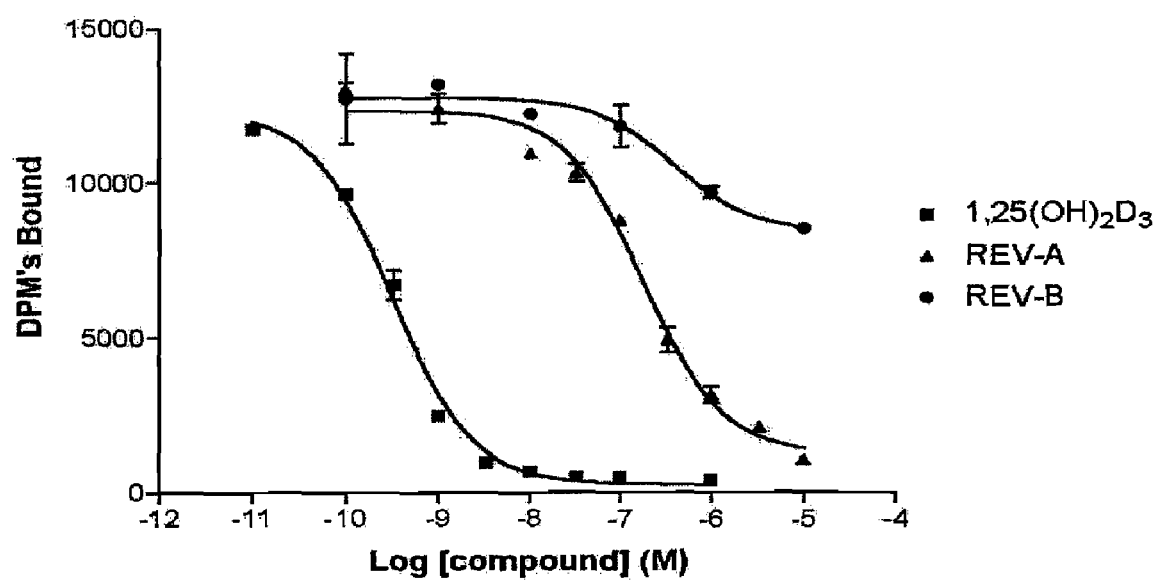
FIGS. 1-6 illustrate various biological activities of 1α,25-dihydroxy-19-norvitamin $D_3$ analog 13, hereinafter referred to as "REV-B," and 3β,25-dihydroxy-19-norvitamin $D_3$ analog 14, hereinafter referred to as "REV-A," as compared to the native hormone 1α,25-dihydroxyvitamin $D_3$, hereinafter "1,25$(OH)_2D_3$."

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. "Alkoxy" refers to any alkyl radical which is attached by oxygen, i.e. a group represented by "alkyl-o-." Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively. An "alkylidene" refers to a radical having the general formula $C_kH_{2k}$— where k is an integer.

The preparation of 19-nor-vitamin D compounds of the basic structures I and II can be accomplished by a common general method, i.e. the Julia olefination involving a coupling of an unsaturated sulfone IV, easily prepared from a bicyclic Windaus-Grundmann type ketone III, with the bicyclic ketone V:

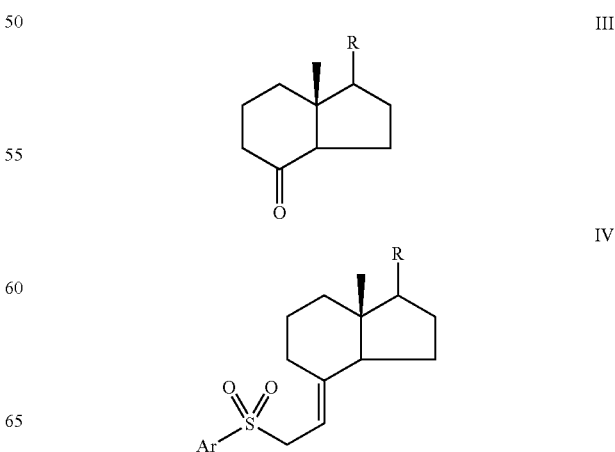

V

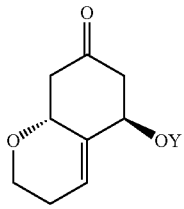

In the structures III, IV and V groups Y and R represent groups defined above whereas Ar represents phenyl, substituted phenyl (preferably phenylthiazoline group) and other aromatic groups that can be suitable for the Julia olefination process, it being also understood that any functionalities in Ar that might be sensitive, or that interfere with the condensation reaction, should be avoided. The process shown above represents an application of the convergent synthesis concept, which has been applied effectively for the preparation of vitamin D compounds (e.g. Kittaka et al, Synlett, 8, 1175 (2003), and J. Org. Chem., 68, 7407 (2003).

Hydrindanones of the general structure III are known, or can be prepared by known methods. Specific important examples of such known bicyclic ketones are the structures with the side chains (a), (b), (c) and (d) described above, i.e. 25-hydroxy Grundmann's ketone (e) [Baggiolini et al., J. Org. Chem, 51, 3098 (1986)]; Grundmann's ketone (f) [Inhoffen et al., Chem. Ber. 90, 664 (1957)]; 25-hydroxy Windaus ketone (g) [Baggiolini et al., J. Org. Chem., 51, 3098 (1986)] and Windaus ketone (h) [Windaus et al., Ann., 524, 297 (1936)]:

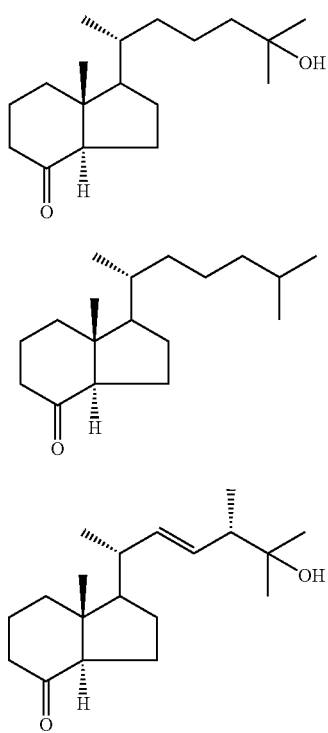

(e)

(f)

(g)

(h)

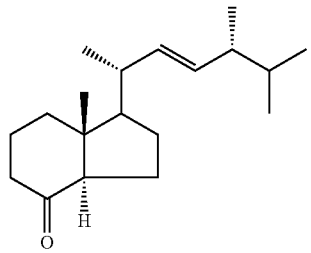

For the preparation of the required bicyclic ketones of general structure V, a new synthetic route has been developed starting from bicyclic lactone 1 that was obtained from commercial (1R,3R,4S,5R)-(−)-quinic acid as described previously [Hanessian et al., J. Org. Chem. 62, 465 (1997)]. First steps of the overall process of transformation of the starting lactone 1 into the desired A-ring synthons, is shown on the SCHEME I. Thus, one of the two secondary hydroxy groups of 1 (equatorial hydroxyl at C-3) was selectively protected as t-butyldimethylsilyl ether (TBDMS) and the other was then oxidized with Dess-Martin periodinane reagent to the 4-ketone 3. The tertiary 1-hydroxyl was acetylated and the resulted acetoxy ketone 4 subjected to the Wittig reaction with an ylide generated from the appropriate phosphonium bromide A, prepared from 3-bromo-1-propanol, and n-butyllithium. This process afforded two isomeric olefinic compounds 5a and 5b in the ratio of ca. 5:1. The subsequent steps of the synthesis are shown on the SCHEME II. Although many different reagents can be used for deprotection of the terminal primary hydroxy group in 5b (e.g. BuSH and $MgBr_2$ in ethyl ether and B-chlorocatecholborane in methylene chloride), a treatment with aluminum iodide in acetonitrile provided the best yield of the desired 3'-hydroxypropylidene compound 6 that was subsequently tosylated under standard conditions. Subsequent reaction of the tosylate 7 with tetrabutylammonium fluoride gave an excellent yield of the cyclized product 8. Its reduction with sodium borohydride furnished a bicyclic triol 9. Periodate cleavage of the vicinal diol and subsequent silylation of the secondary axial hydroxyl in the formed hydroxy ketone 10 provided the desired A-ring fragment 11. This hexahydrochromenone derivative was then subjected to modified Julia olefination. The thiazoline sulphone 12 was synthesized from the Grundmann ketone 15. The synthetic path is described on SCHEME III, and it started from conversion of 15 to the allylic ester 16, that was then reduced to the allylic alcohol 17. This latter compound was subjected to the three-step reaction sequence involving Mitsunobu reation, oxidation and silylation. Coupling of the ketone 11 with the anion generated from 12 and lithium bis(trimethylsilyl)amide, followed by removal of the silyl protecting groups gave the expected mixture of two 19-nor-vitamin D analogs 13 and 14 which were purified and separated by straight- and reversed-phase HPLC. Analysis of their $^1$H NMR spectra confirmed that ring A in these compounds, due to the presence of an exocyclic double bond being a part of additional six-membered ring, is prevented from flipping and held in the single chair conformation.

Several other 19-nor-vitamin D compounds may be synthesized by the method disclosed herein using the A-ring synthon 11 and the appropriate Windaus-Grundmann ketones having the desired side chain structure.

This invention is described by the following illustrative examples. In these examples specific products identified by Arabic numerals (e.g. 1, 2, 3, etc) refer to the specific structures so identified in the preceding description and in the SCHEME I, SCHEME II, and SCHEME III.

EXAMPLES

Chemistry. Melting points (uncorrected) were determined on a Thomas-Hoover capillary melting-point apparatus. Ultraviolet (UV) absorption spectra were recorded with a Perkin-Elmer Lambda 3B U-VIS spectrophotometer in ethanol. $^1$H nuclear magnetic resonance (NMR) spectra were recorded at 400 and 500 MHz with a Bruker Instruments DMX-400 and DMX-500 Avance console spectrometers in deteriochloroform. $^{13}$C nuclear magnetic resonance (NMR) spectra were recorded at 125 MHz with a Bruker Instruments DMX-500 Avance console spectrometer in deuteriochloroform. Chemical shifts (δ) are reported downfield from internal Me$_4$Si (δ0.00). Electron impact (EI) mass spectra were obtained with a Micromass AutoSpec (Beverly, Mass.) instrument. High-performance liquid chromatography (HPLC) was performed on a Waters Associates liquid chromatograph equipped with a Model 6000A solvent delivery system, a Model U6K Universal injector, and a Model 486 tunable absorbance detector. THF was freshly distilled before use from sodium benzophenone ketyl under argon.

Example I

Preparation of 1α,25-dihydroxy- and 3β,25-dihydroxy-19-norvitamin D$_3$ analogs 13 and 14.

Referring first to SCHEME I the starting bicyclic lactone 1 was obtained from commercial (–)-quinic acid as described previously [Hanessian et al., J. Org. Chem. 62, 465 (1997)].

(a) Protection of 3-Hydroxy Group in the Lactone 1.

(1R,3R,4S,5R)-1,4-Dihydroxy-3-[(tert-butyldimethylsilyl)oxy]-6-oxa-bicyclo[3.2.1]octan-7-one (2). To a stirred solution of lactone 1 (1.80 g, 10.34 mmol) and imidazole (2.63 g, 38.2 mmol) in anhydrous DMF (14 mL) was added t-butyldimethylsilyl chloride (1.80 g, 11.9 mmol) at 0° C. The mixture was stirred at 0° C. for 30 min and 1 h at room temperature, poured into water and extracted with ethyl acetate and ether. The organic layer was washed several times with water, dried (MgSO$_4$), and evaporated to give a colorless crystalline residue which was crystallized from hexane/ethyl acetate to give 2.12 g of pure 2. The mother liquors were evaporated and purified by flash chromatography. Elution with hexane/ethyl acetate (8:2) gave additional quantity of crystalline monoether 2 (0.14 g, overall yield 76%) and some quantity of crystalline isomeric (3-OH, 4-OTBDMS) ether (0.10 g, 3%).

2: m.p. 90-94° C. (from hexane); $[α]^{24}_D$ –44° (c 1.00 CHCl$_3$); $^1$H NMR (500 MHz, CDCl$_3$) δ 0.095 (6H, s, 2×SiCH$_3$), 0.901 (9H, s, Si-t-Bu), ca. 2.0 (2H, br m, 2α- and 2β-H), 2.29 (1H, ddd, J=11.6, 6.0, 2.6 Hz, 8β-H), 2.63 (1H, d, J=11.6 Hz, 8α-H), 3.89 (1H, ddd, J=10.4, 7.0, 4.5 Hz, 3β-H), 3.98 (1H, t, J=4.6 Hz, 4β-H), 4.88 (1H, dd, J=6.0, 4.8 Hz, 5α-H); $^{13}$C NMR (125 MHz) δ –5.0 (Si—CH$_3$), –4.7 (Si—CH$_3$), 17.9 [$\underline{C}$(CH$_3$)$_3$], 25.6 [C($\underline{C}$H$_3$)$_3$], 36.4 (C$_8$), 40.2 (C$_2$), 65.8 (C$_4$), 67.0 (C$_3$), 71.9 (C$_1$), 76.3 (C$_5$), 177.9 (C=O), MS (EI) m/z (relative intensity) 288(M$^+$, 1), 231 (41), 213 (21), 185 (85), 75 (100); HRMS (ESI), exact mass calcd for C$_{13}$H$_{24}$O$_5$SiNa (M$^+$+Na) 311.1291, measured 311.1287; Anal. Calcd for C$_{13}$H$_{24}$O$_5$Si: C, 54.14, H, 8.39. Found: C, 53.94, H, 8.36.

(b) Oxidation of 4-Hydroxy Group in the Dihydroxy Lactone 2.

(1R,3R,5R)-3-[(tert-Butyldimethylsilyl)oxy]-1-hydroxy-6-oxa-bicyclo[3.2.1]octane-4,7-dione (3). To a stirred suspension of Dess-Martin periodinane reagent (6.60 g, 15.5 mmol) in anhydrous CH$_2$Cl$_2$ (100 mL) was added compound 2 (3.86 g, 13.4 mmol). The mixture was stirred at room temperature for 18 h, poured into water and extracted with ethyl acetate. The organic layer was washed several times with water, dried (MgSO$_4$), and evaporated to give an oily residue which slowly crystallized on cooling (3.67 g, 95%). TLC indicated high purity of the obtained ketone 3 which could be used in the next step without further purification. Analytical sample was obtained by recrystallization from hexane.

3: m.p. 92-95° C.; $^1$H NMR (400 MHz, CDCl$_3$) δ 0.040 and 0.133 (3H and 3H, each s, 2×SiCH$_3$), 0.895 (9H, s, Si-t-Bu), 2.15 (1H, dd, J=12.4, 10.4 Hz, 2α-H), 2.42 (1H, d, J=12.5 Hz, 8α-H), 2.54 (1H, ddd, J=12.4, 9.0, 3.9 Hz, 2β-H), 2.86 (1H, ddd, J=12.5, 6.7, 3.9 Hz, 8β-H), 4.54 (1H, dd, J=10.4, 9.0 Hz, 3β-H), 4.73 (1H, d, J=6.7 Hz, 5α-H); $^{13}$C NMR (125 MHz) δ –5.6 (Si—CH$_3$), –4.8 (Si—CH$_3$), 18.2 [$\underline{C}$(CH$_3$)$_3$], 25.6 [C($\underline{C}$H$_3$)$_3$], 42.3 (C$_8$), 43.0 (C$_2$), 70.3 (C$_3$), 71.8 (C$_1$), 78.7 (C$_5$), 177.1 (C=O), 202.4 (C$_4$); MS (EI) m/z (relative intensity) no M$^+$, 271 (M$^+$–CH$_3$, 4), 229 (92), 201 (28), 157 (100); HRMS (ESI) exact mass calcd for C$_9$H$_{13}$O$_5$Si (M$^+$-t-Bu) 229.0532, measured 229.0539; Anal. Calcd for C$_{13}$H$_{22}$O$_5$Si×H$_2$O: C, 51.29, H, 7.95. Found: C, 51.09, H, 7.90.

(c) Acetylation of 1-Hydroxy Group in the Hydroxy Ketone 3.

(1R,3R,5R)-1-Acetoxy-3-[(tert-butyldimethylsilyl)oxy]-6-oxa-bicyclo[3.2.1]octane-4,7-dione (4). Solution of hydroxy ketone 3 (1.64 g, 5.8 mmol) in anhydrous pyridine (12 mL) and acetic anhydride (5.5 mL) was stirred for 3 h at room temperature. It was poured into water and extracted with ethyl acetate. The organic layer was washed with saturated NaHCO$_3$, saturated CuSO$_4$ and water, dried (MgSO$_4$), and evaporated to give an oily residue which was dissolved in hexane/ethyl acetate (8:2) and filtered through short path of silica gel. Evaporation of solvents gave pure crystalline acetate 4 (1.51 g, 81%). Analytical sample was obtained by recrystallization from hexane/ethyl acetate.

4: m.p. 134-7° C.; $[α]^{24}_D$ –78° (c 1.00 CHCl$_3$); $^1$H NMR (400 MHz, CDCl$_3$) δ 0.046 and 0.141 (3H and 3H, each s, 2×SiCH$_3$), 0.901 (9H, s, Si-t-Bu), 2.17 (3H, s, CH$_3$CO), 2.28 (1H, dd, J=12.2, 10.4 Hz, 2α-H), 2.32 (1H, d, J=12.1 Hz, 8β-H), 2.65 (1H, ddd, J=12.2, 8.8, 3.9 Hz, 2β-H), 3.56 (1H, ddd, J=12.1, 6.9, 3.9 Hz, 8β-H), 4.58 (1H, dd, J=10.4, 8.8 Hz, 3β-H), 4.80 (1H, d, J=6.9 Hz, 5α-H); $^{13}$C NMR (125 MHz) δ –5.8 (Si—CH$_3$), –4.9 (Si—CH$_3$), 18.2 [$\underline{C}$(CH$_3$)$_3$], 20.9 ($\underline{C}$H$_3$—C=O), 25.6 [C($\underline{C}$H$_3$)$_3$], 38.3 (C$_8$), 40.3 (C$_2$), 70.4 (C$_3$), 75.3 (C$_1$), 78.4 (C$_5$), 169.1 (CH$_3$—$\underline{C}$=O), 171.5 (C=O), 201.8 (C$_4$); MS (EI) m/z (relative intensity) 328 (M$^+$, 6), 271 (100), 256 (38), 229 (54), 211 (53); HRMS (ESI) exact mass calcd for C$_{11}$H$_{15}$O$_6$Si (M$^+$-t-Bu) 271.0638, measured 271.0646; Anal. Calcd for C$_{15}$H$_{24}$O$_6$Si: C, 54.86, H, 7.37. Found: C, 54.88, H, 7.37.

(d) Preparation of the Phosphonium Bromide A.

[3-(Methoxymethoxy)propyl]triphenylphosphonium bromide (A). To a solution of bromomethyl methyl ether (1.3 mL, 16 mmol) and N,N-diisopropylethylamine (4.5 mL, 27.7 mmol) in anhydrous CH$_2$Cl$_2$ (50 mL) at 0° C. was added 3-bromo-1-propanol (1.0 mL, 11 mmol) and the mixture was stirred at 0° C. for 1 h and at room temperature for 20 h. The reaction mixture was poured into 1 N HCl (150 mL), organic phase was separated and water phase was extracted with CH$_2$Cl$_2$. The combined organic phases were washed with water and diluted NaHCO$_3$, dried (MgSO$_4$), and evaporated to give a yellowish oil. The residue was purified by flash chromatography. Elution with hexane/ethyl acetate (95:5) afforded pure oily 1-bromo-3-(methoxymethoxy)propane (1.12 g, 55%):

$^1$H NMR (400 MHz, CDCl$_3$) δ 2.13 (2H, m, CH$_2$—CH$_2$—CH$_2$), 3.37 (3H, s, O—CH$_3$), 3.53 (2H, br t, J=6.5 Hz, Br—CH$_2$), 3.67 (2H, br t, J=5.8 Hz, CH$_2$—CH$_2$—O), 4.63 (2H, s, O—CH$_2$—O).

To a solution of 1-bromo-3-(methoxymethoxy)propane (0.46 g, 2.5 mmol) in anhydrous toluene (1.5 mL) was added triphenylphoshine (0.71 g, 2.7 mmol) under argon with stirring. The mixture was heated at 100° C. for 20 h and cooled to room temperature. The liquid was decanted and the solid residue was grounded with spatula, filtered and washed several times with ether. After drying overnight in vacuum dessicator colorless crystals of phosphonium salt A (0.98 g, 88%) could be used in the Wittig reaction without further purification.

A: m.p. 165-168° C., $^1$H NMR (500 MHz, CDCl$_3$) δ 1.96 (2H, m, CH$_2$—CH$_2$—CH$_2$), 3.31 (3H, s, O—CH$_3$), 3.85 (2H, br t, J=5.6 Hz, CH$_2$—CH$_2$—O), 4.00 (2H, m, P—CH$_2$), 4.60 (2H, s, O—CH$_2$—O), 7.70, 7.79 and 7.86 (6H, 3H and 6H, each m, Ar—H); Anal. Calcd for C$_{23}$H$_{26}$O$_2$PBr: C, 62.03, H, 5.88, Br, 17.94. Found: C, 61.87, H, 5.77, Br, 17.89.

(e) Wittig Reaction of the 4-Ketone 4 with the Ylide Generated from A.

[(E)- and (Z)-(1R,3R,5R)-1-Acetoxy-3-[(tert-butyldimethylsilyl)oxy]-6-oxa-4-[3'-(methoxymethoxy)propylidene]bicyclo[3.2.1]octan-7-one (5a and 5b). To the phosphonium bromide A (420 mg, 0.94 mmol) in anhydrous THF (5 mL) at 0° C. was added dropwise n-BuLi (1.6 M in hexanes, 1.12 mL, 1.8 mmol) under argon with stirring. After 5 min another portion of A was added (420 mg, 0.94 mmol) and the solution was stirred at 0° C. for 10 min and then at room temperature for 20 min. The orange-red mixture was cooled to –78° C. and siphoned in 2 equal portions (30 min interval) to a solution of keto lactone 4 (300 mg, 0.91 mmol) in anhydrous THF (8 mL). The reaction mixture was stirred at –78° C. and stopped by addition of brine cont. 1% HCl (3 h after addition of the first portion of the Wittig reagent). Ethyl acetate (9 mL), benzene (6 mL), ether (3 mL), sat. NaHCO$_3$ (3 mL), and water (3 ml) were added and the mixture was vigorously stirred at room temperature for 18 h. Then an organic phase was separated, washed with brine, dried (MgSO$_4$), and evaporated. The oily residue (consisting mainly with isomeric 5a and 5b in the ratio of ca. 5:1) was separated by flash chromatography on silica. Elution with hexane/ethyl acetate (85:15) resulted in partial separation of products: 29 mg of 5b, mixture of 5a and 5b (85 mg) and pure 5a (176 mg; total yield 77%). Rechromatography of the mixed fractions resulted in almost complete separation of the products.

5a: [α]$^{24}_D$–63° (c 0.60 CHCl$_3$); $^1$H NMR (500 MHz, CDCl$_3$) δ 0.074 (6H, s, 2×SiCH$_3$), 0.914 (9H, s, Si-t-Bu), 2.13 (3H, s, OCH$_3$), 2.00 (1H, brt, J=11.2, Hz, 2β-H), 2.10 (1H, d, J=10.8 Hz, 8α-H), 2.34 (1H, ddd, J=11.7, 7.0, 2.9 Hz, 2β-H), 2.38 and 2.43 (1H and 1H, each m, =C—CH$_2$), 3.31 (1H, ddd, J=10.8, 6.5, 2.9 Hz, 8, —H), 3.35 (3H, s, O—CH$_3$), 3.54 and 3.60(1H and 1H, each m, CH$_2$—CH$_2$—O), 4.41 (1H, t, J=8.2 Hz, 3β-H), 4.60 (2H, s, O—CH$_2$—O), 5.52 (1H, d, J=6.5 Hz, 5α-H), 5.71 (1H, br t, J=7.1 Hz, =CH); $^{13}$C NMR (125 MHz) 6-5.1 (Si—CH$_3$), –4.9 (Si—CH$_3$), 18.1 [C(CH$_3$)$_3$], 21.1 CH$_3$—C=O), 25.7 [C(CH$_3$)$_3$], 27.5 (CH$_2$—CH$_2$—C=), 40.5 (C$_8$), 41.5 (C$_2$), 55.2 (O—CH$_3$), 66.7 (O—CH$_2$—CH$_2$), 66.8 (C$_3$), 77.1 (C$_1$), 73.9 (C$_5$), 96.3 (O—CH$_2$—O), 121.9 (=C—CH$_2$), 136.8 (C$_4$), 169.1 (CH$_3$—C=O), 172.9 (C=O); MS (EI) m/z (relative intensity), no M$^+$, 383 (M$^+$–OCH$_3$, 3), 357 (10), 325 (44), 297 (12), 267 (15), 265 (40), 237 (89), 75 (100); HRMS (ESI) exact mass calcd for C$_{20}$H$_{34}$O$_7$SiNa (M$^+$+Na) 437.1972, measured 437.1975.

5b: $^1$H NMR (500 MHz, CDCl$_3$) δ 0.108 and 0.125 (3H and 3H, each s, 2×SiCH$_3$), 0.912 (9H, s, Si-t-Bu), 2.13 (3H, s, OCH$_3$), 2.15 (1H, dd, J=12.6, 8.3 Hz, 2α-H), 2.31 (1H, d, J=10.8 Hz, 8α-H), 2.33 (1H, 2β-H overlapped with 8α-H), 2.67 and 2.73 (1H and 1H, each m, =C—CH$_2$), 3.25 (1H, ddd, J=10.8, 6.3, 2.8 Hz, 8β-H), 3.36 (3H, s, O—CH$_3$), 3.55 (2H, m, CH$_2$—CH$_2$—O), 4.61 (2H, s, O—CH$_2$—O), 4.71 (1H, br t, J~7 Hz, 3β-H), 4.94 (1H, d, J=6.3 Hz, 5α-H), 5.64 (1H, dt, J=1.7, 7.1 Hz, =CH); $^{13}$C NMR (125 MHz) δ –4.6 (Si—CH$_3$), –4.5 (Si—CH$_3$), 17.9 [C(CH$_3$)$_3$], 21.1 ( CH$_3$—C=O), 25.7 [C(CH$_3$)$_3$], 27.8 (CH$_2$—CH$_2$—C=), 38.9 (C$_8$), 41.2 (C$_2$), 55.3 (O—CH$_3$), 67.1 (O—CH$_2$—CH$_2$), 67.2 (C$_3$), 77.1 (C$_1$), 81.8 (C$_5$), 96.4 (O—CH$_2$—O), 128.9 (=C—CH$_2$), 134.8 (C$_4$), 169.1 (CH$_3$—C=O), 173.0 (C=O); MS (EI) m/z (relative intensity), no M$^+$, 383 (M$^+$–OCH$_3$, 2), 357 (2), 325 (22), 297 (17), 267 (35), 265 (14), 237 (96), 75 (100); HRMS (ESI) exact mass calcd for C$_{20}$H$_{34}$O$_7$SiNa (M$^+$+Na) 437.1972, measured 437.1974.

(4Z)-(1R,3R,5R)-1-Acetoxy-3-[(tert-butyldimethylsilyl)oxy]-4-[3'-hydroxypropylidene]-6-oxabicyclo[3.2.1]octan-7-one (6). To a solution of 5b (26 mg, 63 μmol) in anhydrous CH$_3$CN (0.6 mL) was added AlI$_3$ (170 mg, 0.42 mmol) at 0° C. under argon. The mixture was stirred at 0° C. for 50 min, poured into aq Na$_2$S$_2$O$_3$, and extracted with ethyl acetate. The extract was washed with brine, dried (Na$_2$SO$_4$) and evaporated. The residue was purified by flash chromatography. Elution with hexane/ethyl acetate (6:4) afforded compound 6 as a colorless oil (16.5 mg, 71%).

6: $^1$H NMR (500 MHz, CDCl$_3$) δ 0.132 and 0.144 (3H and 3H, each s, 2×SiCH$_3$), 0.925 (1H, s, C(CH$_3$)$_3$), 2.13 (3H, s, COCH$_3$), 2.14 (1H, dd, J=12.4, 8.8 Hz, 2α-H), 2.28 (1H, d, J=10.8 Hz, 8α-H), 2.33 (1H, ddd, J=12.4, 7.0, 2.8 Hz, 2β-H), 2.45 and 2.79 (2H, 2×m, CH—CH$_2$), 3.29 (1H, ddd, J=10.8, 6.2, 2.8 Hz, 8β-H), 3.60 and 3.71(2H, 2×m, CH$_2$OH), 4.71 (1H, t, J=7.8 Hz, 3β-H), 4.97 (1H, d, J=6.3 Hz, 5α-H), 5.65 (1H, dt, J=1.8, 7.8 Hz, =CH); $^{13}$C NMR (125 MHz) δ –4.6 (SiCH$_3$), 17.9 [C(CH$_3$)$_3$], 25.8 [C(CH$_3$)$_3$], 21.1 (COCH$_3$), 30.1 (CH—CH$_2$), 39.8 (C$_8$), 41.4 (C$_2$), 61.4 (CH$_2$OH), 67.6 (C$_3$), 77.0 (C$_1$), 81.2 (C$_5$), 128 (CH—CH$_2$), 135.8 (C$_4$), 169.2 (COCH$_3$), 173.0 (CO); HRMS (ESI) exact mass calcd for C$_{18}$H$_{30}$O$_6$SiNa (M$^+$+Na) 393.1709, measured 393.1690.

(4Z)-(1R,3R,5R)-1-Acetoxy-3-[(tert-butyldimethylsilyl)oxy]-6-oxa-4-[3'-(p-toluenesulfonyloxy)propylidene]bicyclo[3.2.1]octan-7-one (7). To a solution of hydroxy compound (16 mg, 43 μmol) in anhydrous pyridine (140 μL) was added at 0° C. p-toluenesulfonyl chloride (24 mg, 127 μmol) and a catalytic quantity of 4-(dimethylamino)pyridine. The mixture was stirred at 0° C. for 1 h and at 6° C. for 18 h. It was then poured into ice/saturated NaHCO$_3$, shaken for 15 min and extracted with ethyl acetate and benzene. The combined extracts were washed with saturated NaHCO$_3$, water, saturated CuSO$_4$, water again, dried (Na$_2$SO$_4$) and evaporated. The residue (ca. 16 mg) was dissolved in benzene/hexane, applied on a silica Sep-Pak cartridge, and washed with hexane/ethyl acetate (95:5, 10 mL) to remove apolar impurities. Elution with washed with hexane/ethyl acetate (85:15, 20 mL) provided a pure oily tosylate 7 (19 mg, 84%).

7: [α]$^{24}_D$–48° (c 0.80 CHCl$_3$); $^1$H NMR (400 MHz, CDCl$_3$) δ 0.043 and 0.088 (3H and 3H, each s, 2×SiCH$_3$), 0.871 (1H, s, C(CH$_3$)$_3$), 2.13 (3H, s, COCH$_3$), 2.08 (1H, dd, J=12.0, 9.3 Hz, 2α-H), 2.16 (1H, d, J=10.8 Hz, 8α-H), 2.28 (1H, ddd, J=12.0, 6.9, 3.0 Hz, 2β-H), 2.46 (3H, s, CH$_3$—Ar), 2.67 and 2.88 (2H, 2×m, CH—CH$_2$), 3.26 (1H, ddd, J=10.8, 6.2, 3.0 Hz, 8-β-H), 4.05 (2H, t, J=6.4 Hz, CH$_2$OS), 4.62 (1H, t, J~8 Hz, 3β-H), 4.85 (1H, d, J=6.4 Hz, 5α-H), 5.43 (1H, dt, J=2, 7.5 Hz, =CH), 7.36 and 7.78 (2H and 2H, each d, J=8.3 Hz, Ar—H); HRMS (ESI) exact mass calcd for C$_{25}$H$_{36}$O$_8$SSiNa (M$^+$+Na) 547.1798, measured 547.1812

(1R,7R,9S)-(9-Acetoxy-6,11-dioxa-tricyclo[7.2.1.0*2,7*]dodec-2-en-10-one (8). Solution of tosylate 7 (18.8 mg, 36 μmol) in dry THF (8 mL) was treated with tetrabutylammonium fluoride (1.0 M in THF, 180 μl, 180 μmol). The mixture was stirred under argon at room temperature for 18 h, poured into brine, and extracted with ethyl acetate and benzene. Organic extracts were washed with brine, dried (Na$_2$SO$_4$) and evaporated. The oily residue was dissolved in hexane and applied on a silica Sep-Pak cartridge, and washed with hexane/ethyl acetate (85:15, 20 mL) to give a pure tricyclic product 8 (7.6 mg, 89%) as an oil.

8: [α]$^{24}_D$ −51° (c 0.40 CHCl$_3$); $^1$H NMR (400 MHz, CDCl$_3$) δ 2.02 (1H, dm, J~17 Hz, 4β-H), 2.07 (1H, dd, J=11.6, 10.6 Hz, 8α-H), 2.11 (1H, d, J=11.0 Hz, 12α-H), 2.13 (3H, s, COCH$_3$), 2.39 (1H, m, w/2=38 Hz, 4α-H), 2.50 (1H, ddd, J=11.6, 7.8, 3.1 Hz, 8β-H), 3.35 (1H, ddd, J=11.0, 6.2, 3.1 Hz, 12β-H), 3.66 (1H, dt, J=3.8, 11.4 Hz, 5β-H), 4.04 (1H, dd, J=11.5, 6.3 Hz, 5α-H), 4.31 (1H, m, w/2=22 Hz, 7β-H), 5.00 (1H, d, J=6.2 Hz, 1α-H), 5.86 (1H, m, w/2=11 Hz, 3-H); $^{13}$C NMR (125 MHz) δ 21.1 (CO<u>C</u>H$_3$), 24.5 (C$_4$), 37.6 (C$_8$), 40.9 (C$_{12}$), 64.2 (C$_5$), 69.1 (C$_7$), 78.5 (C$_1$), 77.1 (C$_9$), 121.9 (C$_3$), 134.6 (C$_2$), 169.2 (<u>C</u>OCH$_3$), 172.5 (C$_{10}$); HRMS (ESI) exact mass calcd for C$_{12}$H$_{14}$O$_5$ (M$^+$) 238.0841, measured 238.0851

(5R,7R,8aR)-7-Hydroxymethyl-3,5,6,7,8,8a-hexahydro-2H-chromene-5,7-diol (9). To a solution of tricyclic compound 8 (9.5 mg, 40 μmol) at 0° C. was added NaBH$_4$. The resultant mixture was then stirred at room temperature for 18 h, a small volume of brine/saturated NH$_4$Cl was added, and the solvents were removed in vacuum. The residue was washed several times with warm ethanol. The ethanol extracts were combined and evaporated to dryness with benzene. The solid residue was then washed few times with warm chloroform. The combined chloroform extracts were concentrated to a small volume and applied on a silica Sep-Pak cartridge. Elution with hexane/ethyl acetate (1:9, 20 mL) yielded a pure semisolid triol 9 (6 mg, 75%).

9: [α]$^{24}_D$+20° (c 0.30, MeOH); $^1$H NMR (500 MHz, CDCl$_3$) δ 1.54 (1H, t, J=12.1 Hz, 8α-H), 1.65 (1H, dd, J=14.3, 3.9 Hz, 6α-H), 1.98 (1H, dm, J~16 Hz, 3β-H), 2.18 (1H, dt, J=14.3, 2.3 Hz, 6β-H), 2.29 (1H, ddd, J=12.4, 5.5, 2.3 Hz, 8β-H), 2.34 (1H, br m, 3α-H), 3.60 (1H, ddd, J=11.2, 10.2, 3.8 Hz, 2β-H), 3.72 and 3.81 (1H and 1H, each d, J=11.3 Hz, CH$_2$OH), 3.94 (1H, ddd, J=11.2, 5.7, 2.0 Hz, 2α-H), 4.37 (2H, m, 5α- and 8aβ-H), 5.84 (1H, m, w/2=11 Hz, 4-H);
$^{13}$C NMR (125 MHz) δ 25.5 (C$_3$), 41.3 and 41.8 (C$_6$ and C$_8$), 62.9 (C$_2$), 69.2 (CH$_2$OH), 69.4 (C$_{8a}$), 72.2 (C$_5$), 76.5 (C$_7$), 122.8 (C$_4$), 140.0 (C$_{4a}$); HRMS (ESI) exact mass calcd for C$_{10}$H$_{14}$O$_3$ (M$^+$-H$_2$O) 182.0943, measured 182.0949.

(5R,8aR)-5-Hydroxy-2,3,5,6,8,8a-hexahydro-chromen-7-one (10): Sodium periodate-saturated water (50 μL) was added to a solution of the triol 21 (5 mg, 2.6 μmol) in methanol (200 μL) at 0° C. The mixture was stirred at 0° C. for 1 h, then thioanisole was added and stirring was continued for 10 min. The mixture was diluted with benzene/ethyl acetate (1:1, 1 mL) and filtered through a silica Sep-Pak. Then Sep-Pak was washed with additional 5 mL of the same solvent system, the combined solutions were evaporated, the residue redissolved in hexane/ethyl acetate (7:3) and applied on a silica gel Sep-Pak. Elution with the same solvent system (10 mL) provided aromatic compounds and a pure (5R,8aR)-5-hydroxy-2,3,5, 6,8,8a-hexahydro-chromen-7-one (4.1 mg, 98%) was eluted with hexane/ethyl acetate (1:1, 10 mL) as a colorless oil.

10: [α]$^{24}_D$+6° (c 0.22, CHCl$_3$); $^1$H NMR (500 MHz, CDCl$_3$) δ 2.09 (1H, dm, J=17.6 Hz, 3α-H), 2.38 (1H, m, w/2=35 Hz, 3β-H), 2.49 (1H, dd, J=13.8, 11.1 Hz, 8α-H), 2.60 (1H, dd, J=15.0, 3.7 Hz, 6α-H), 2.65 (1H, dd, J=15.0, 2.5 Hz, 6β-H), 2.89 (1H, ddd, J=13.8, 6.4, 1.6 Hz, 8β-H), 3.68 (1H, ddd, J=11.3, 9.3, 3.9 Hz, 2β-H), 3.96 (1H, ddd, J=11.3, 5.4, 2.9 Hz, 2α-H), 4.62 (1H, t, J~3 Hz, 5α-H), 4.67 (1H, m, w/2=24 Hz, 8aβ-H), 6.01 (1H, m, w/2=10 Hz, 4-H); $^{13}$C NMR (125 MHz) δ 25.1 (C$_3$), 47.9 (C$_8$), 48.8 (C$_6$), 62.5 (C$_2$), 69.9 (C$_{8a}$), 72.5 (C$_5$), 123.3 (C$_4$), 138.2 (C$_{4a}$), 206.5 (C$_7$); HRMS (ESI) exact mass calcd for C$_9$H$_{12}$O$_3$Na (M$^+$+Na) 191.0684, measured 191.0676.

(5R,8aR)-5-[tert-Butyldimethylsilyl)oxy]-2,3,5,6,8,8a-hexahydro-chromen-7-one (11). To a solution of hydroxy ketone (4 mg, 24 μmol) in anhydrous methylene chloride (90 μl) was added at −50° C. 2,6-lutidine (7 μL, 60 mmol) and tert-butyldimethylsilyl trifluoromethanesulfonate (12 μL, 51 mmol). The reaction mixture was stirred at −50° C. for 50 min, diluted with cold methylene chloride and poured into water. The organic phase was washed with saturated CuSO$_4$ and water, dried (Na$_2$SO$_4$) and evaporated. The residue was redissolved in hexane and applied on a silica gel Sep-Pak. Elution with hexane/ethyl acetate (95:5, 10 mL) provided less polar compound (2.1 mg) being TBDMS derivative of the enol ether derived from 11. The desired protected hydroxy ketone 11 (3.3 mg, 49%) was eluted with hexane/ethyl acetate (9:1, 10 mL) as a colorless oil. Further elution with the same solvent system afforded 2,3,8,8a-tetrahydro-chromen-7-one (0.6 mg).

11: [α]$^{24}_D$−9° (c 0.11, CHCl$_3$); $^1$H NMR (500 MHz, CDCl$_3$) δ 0.035 and 0.058 (3H and 3H, each s, 2×SiCH$_3$), 0.838 [1H, s, C(CH$_3$)$_3$], 2.08 (1H, dm, J=17.3 Hz, 3α-H), 2.33 (1H, m, w/2=33 Hz, 3β-H), 2.46 (1H, dd, J=14.0, 10.9 Hz, 8α-H), 2.53 (2H, narr m, 6α- and 6β-H), 2.86 (1H, br dd, J=14.0, 6.5 Hz, 8β-H), 3.65 (1H, ddd, J=11.4, 9.0, 3.9 Hz, 2β-H), 3.92 (1H, ddd, J=11.4, 4.9, 3.7 Hz, 2α-H), 4.51 (1H, t, J~3 Hz, 5α-H), 4.61 (1H, m, w/2=22 Hz, 8aβ-H), 5.87 (1H, m, w/2=10 Hz, 4-H); HRMS (ESI) exact mass calcd for C$_{15}$H$_{26}$O$_3$SiNa (M$^+$+Na) 305.1549, measured 305.1534.

[(1R,3aS,7aR)-7a-Methyl-1-[(R)-6-[(triethylsilyl)oxy]-6-methylheptan-2-yl]-octahydro-inden-(4E)-ylidene]acetic acid ethyl ester (16): To a suspension of NaH (49 mg, 2.04 mmol) in anhydrous THF (1.2 mL) was added (EtO)$_2$P(O)CH$_2$COOEt (500 ml, 2.53 mmol) at 0° C. The mixture was stirred at room temperature for 10 min and lithium chloride (13 mg, 0.30 mmol) was then added. The stirring was continued for 1 h, cooled to 0° C. and a solution of the protected hydroxy ketone 15 (100 mg, 0.25 mmol) in THF (0.6 mL) was added. After stirring at room temperature for 70 h the reaction mixture was diluted with ethyl acetate and poured into saturated ammonium chloride. Organic phase was separated, washed with brine, dried (Na$_2$SO$_4$) and evaporated. The residue was separated by flash chromatography. Elution with hexane/ethyl acetate (99:1) afforded pure oily [(1R,3aS,7aR)-7a-methyl-1-[(R)-6-[(triethylsilyl)oxy]-6-methylheptan-2-yl]-octahydro-inden-(4E)-ylidene]acetic acid ethyl ester 16 (61 mg, 52%, 65% based on recovered starting material). Further elution with hexane/ethyl acetate (97:3) gave unchanged substrate 15 (20 mg).

16: $^1$H NMR (400 MHz, CDCl$_3$) δ 0.562 (6H, q, J=7.9 Hz, 3×SiCH$_2$), 0.581 (3H, s, 7a-H$_3$), ca. 0.94 (3H, overlapped, CH$_3$—CH), 0.944 (9H, t, J=7.9 Hz, 3×SiCH$_2$CH$_3$), 1.187 [6H, s, C(CH$_3$)$_2$], 1.284 (3H, t, J=7.1 Hz, CH$_3$CH$_2$O), 3.84 (1H, m, 5β-H), 4.15 (2H, m, CH$_3$CH$_2$O), 5.45 (1H, br s, =CH).

2-[(1R,3 aS,7aR)-7a-Methyl-[(R)-6-[(triethylsilyl)oxy]-6-methylheptan-2-yl]-octahydro-inden-(4E)-ylidene]ethanol (17). Diisobutylaluminum hydride (1 M in toluene, 200 μL, 0.2 mmol) was added to a stirred solution of allylic ester (29 mg, 62 μmol) in anhydrous toluene (0.5 mL) at −78° C.

under argon. The mixture was stirred at −78° C. for 1 h, and the reaction was quenched by addition of potassium sodium tartrate (2 N, 1 mL), aq HCl (2 N, 1 mL), and water (12 mL). The mixture was poured into brine and extracted with ethyl acetate and ether. The combined extracts were washed with diluted $NaHCO_3$ and brine, dried ($Na_2SO_4$) and evaporated. The residue was redissolved in hexane and applied on a silica gel Sep-Pak. Elution with hexane/ethyl acetate (95:5, 20 mL, and 9:1, 10 mL) gave allylic alcohol 17 (23 mg, 87%) as a colorless oil.

17: $^1$H NMR (400 MHz, $CDCl_3$) δ 0.563 (6H, q, J=7.9 Hz, 3×$SiCH_2$), 0.554 (3H, s, 7a-$H_3$), 0.928 (3H, d, J=7 Hz, $CH_3$—CH), 0.945 (9H, t, J=7.9 Hz, 3×$SiCH_2CH_3$), 1.188 [6H, s, C($CH_3$)$_2$], 2.63 (1H, dd, J=12.0, 4.5 Hz, 5β-H), 4.20 (2H, m; after $D_2O$ d, J=7.0 Hz, $CH_2OH$), 5.22 (1H, t, J=7.0 Hz, =CH).

(1R,3aS,7aR)-4-[2-(Benzothiazole-2-sulfonyl)-(4E)-ethylidene]-7a-methyl-1-[(R)-6-[(triethylsilyl)oxy]-6-methylheptan-2-yl]-octahydro-indene (12). To a solution of 2-mercaptobenzotriazole (12.5 mg, 75 μmol) and $Ph_3P$ (19.5 mg, 75 μmol) in dry methylene chloride (150 μL) at 0° C. was added a solution of allylic alcohol 17 (21 mg, 50 μmoL) in methylene chloride (150 μL) followed by DIAD (14 μL, 50 μmol). The mixture was stirred at 0 oC for 1 h and the solvents were evaporated in vacuo. The residue was dissolved in ethanol (300 mL), cooled to 0° C. and 30% $H_2O_2$ (30 μL) was added, followed by ammonium ($NH_4$)$_6$$MoO_7O_{24}$×$4H_2O$ (12.3 mg, 10% mol). The mixture was stirred at room temperature for 3 h, poured into cold saturated $Na_2SO_3$ and extracted with ethyl acetate. The organic layer was washed with brine, dried ($Na_2SO_4$) and evaporated. The residue was dissolved in small volume of benzene/hexane (1:1) and applied on a silica Sep-Pak. Elution with hexane/ethyl acetate (9:1, 20 mL and 85:15, 20 mL) and removal of the solvents gave an oily product (33 mg) that was dissolved in anhydrous DMF (300 μL). Imidazole (18 mg, 0.26 mmol) was added followed by triethylsilyl chloride (50 μL, 0.29 mmol) and the mixture was stirred at room temperature for 3 h. Ethyl acetate was added and water, and the organic layer separated, washed with brine, dried ($Na_2SO_4$) and evaporated. The residue was purified by HPLC (10 mm×25 cm Zorbax-Sil column, 4 mL/min) using hexane/ethyl acetate (9:1) solvent system. Analytically pure sulfone 12 (22.8 mg, 76%) was collected at Rv 24 mL.

12: $^1$H NMR (400 MHz, $CDCl_3$) δ 0.262 (3H, s, 7a-$H_3$), 0.552 (6H, q, J=7.9 Hz, 3×$SiCH_2$), 0.852 (3H, d, J=6.2 Hz, $CH_3$—CH), 0.935 (9H, t, J=7.9 Hz, 3×$SiCH_2CH_3$), 1.173 [6H, s, C($CH_3$)$_2$], 2.55 (1H, br d, J=13 Hz, 5β-H), 4.21 (1H, dd, J=14.2, 6.9 Hz, one of $CH_2S$), 4.43 (1H, dd, J=14.2, 8.9 Hz, one of $CH_2S$), 5.02 (1H, t, J=7.8 Hz, =CH), 7.61 (2H, m, Ar—H), 8.00 and 8.22 (1H and 1H, each d, J=8.0 Hz, Ar—H).

1α,25-Dihydroxy- and 3β,25-dihydroxy-19-norvitamin $D_3$ analogs (13 and 14). To a solution of sulfone 12 (20.7 mg, 34 μmol) in dry THF (150 μL) was added LiHMDS (1 M in THF, 32 μL, 32 μmol) at −78° C. under argon. The solution turned deep red. The mixture was stirred at −78° C. for 1 h and a solution of the ketone 11 (2.0 mg, 7.1 μmol) in THF (100 μL) was added. The stirring was continued at −78° C. for 2 h, and the reaction mixture was allowed to warm slowly (for 4 h) to 0° C. After stirring for an additional 30 min at 0° C. it was poured into saturated $NH_4Cl$ and extracted with ether. The extract was washed with brine, dried ($Na_2SO_4$) and evaporated. The yellow oily residue was dissolved in hexane and applied on a silica Sep-Pak. Elution with hexane/ethyl acetate (99.5:0.5, 10 mL and 99:1, 10 mL) and removal of solvents provided the oily residue containing silylated 19-norvitamins (ca. 0.5 mg). The residue was dissolved in dry THF (200 μL) containing $Et_3N$ (3 μL) and treated with tetrabutylammonium fluoride (1.0 M in THF, 20 μl, 20 μmol). The mixture was stirred under argon at room temperature for 17 h, poured into brine, and extracted with ethyl acetate. Organic extract was washed with brine, dried ($Na_2SO_4$) and evaporated. The residue was purified by HPLC (10 mm×25 cm Zorbax-Sil column, 4 mL/min) using hexane/2-propanol (9:1) solvent system. Isomeric 19-norvitamins 13 and 14 (0.2 mg, 6%) were collected at Rv 35 mL and Rv 37 mL. Final purification and separation of both isomers was achieved by reversed-phase HPLC (6.2 mm×25 cm Zorbax-ODS column, 2 mL/min) using methanol/water (9:1) solvent system. 1α,25-dihydroxyvitamin D analog 13 (120 μg) was collected at Rv 22.5 mL and its isomer 14 (72 μg) at Rv 17.5 mL.

13: UV (in EtOH) $λ_{max}$ 242.0, 251.0, 261.5 nm; $^1$H NMR (500 MHz, $CDCl_3$) δ 0.548 (3H, s, 18-$H_3$), 0.938 (3H, d, J=6.2 Hz, 21-$H_3$), 1.219 (6H, s, 26- and 27-$H_3$), 2.69 (1H, dd, J=11.7, 6.3 Hz, 4α-H), 2.83 (1H, br d, J~10 Hz, 9β-H), 3.05 (1H, d, J=14.5 Hz, 10α-H), 3.62 (1H, dt, J=10.5, 3.4 Hz, one of $CH_2$—C$\underline{H}_2$—O), 3.93 (1H, m, w/2=22 Hz, one of $CH_2$—C$\underline{H}_2$—O), 4.30 (1H, m, w/2=25 Hz, 3α-H), 4.34 (1H, br s, 1β-H), 5.82 (1H, narr m, $\underline{H}C$=C—$CH_2$), 5.83 and 6.47 (1H and 1H, each d, J=11.0 Hz, 7- and 6-H); HRMS (ESI) exact mass calcd for $C_{29}H_{46}O_3Na$ ($M^+$+Na) 465.3345, measured 465.3346.

14: UV (in EtOH) $λ_{max}$ 242.5, 251.0, 261.0 nm; $^1$H NMR (500 MHz, $CDCl_3$) δ 0.551 (3H, s, 18-$H_3$), 0.939 (3H, d, J=6.2 Hz, 21-$H_3$), 1.220 (6H, s, 26- and 27-$H_3$), 2.42 and 2.47 (1H and 1H, each d, J=13.5 Hz, 4α- and 4β-H), 2.82 (1H, br d, J=10.3 Hz, 9β-H), 3.24 (1H, dd, J=12.0, 5.6 Hz, 10β-H), 3.64 and 3.96 (1H and 1H, each m, $CH_2$—C$\underline{H}_2$—O), 4.29 (2H, m, 1β-H overlapped with 3α-H), 5.84 (1H, m, w/2~15 Hz, $\underline{H}C$=C—$CH_2$), 5.93 and 6.33 (1H and 1H, each d, J=10.5 Hz, 7- and 6-H); HRMS (ESI) exact mass calcd for $C_{29}H_{46}O_3Na$ ($M^+$+Na) 465.3346, measured 465.3350.

SCHEME I

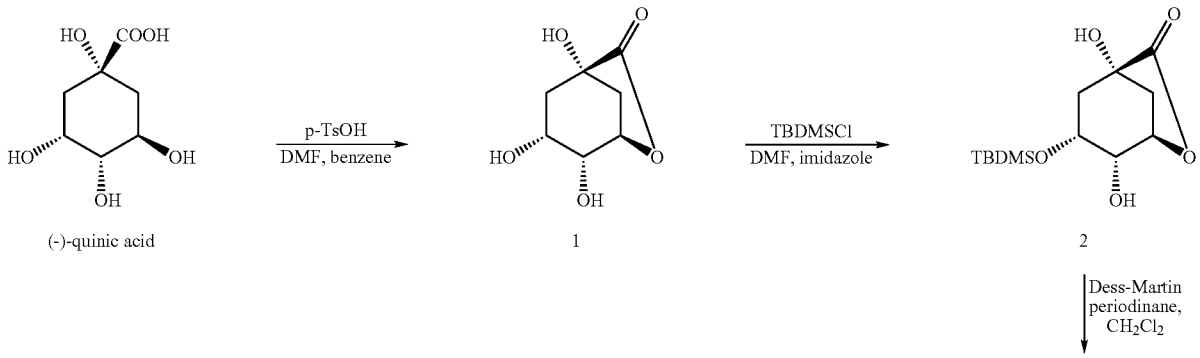

-continued
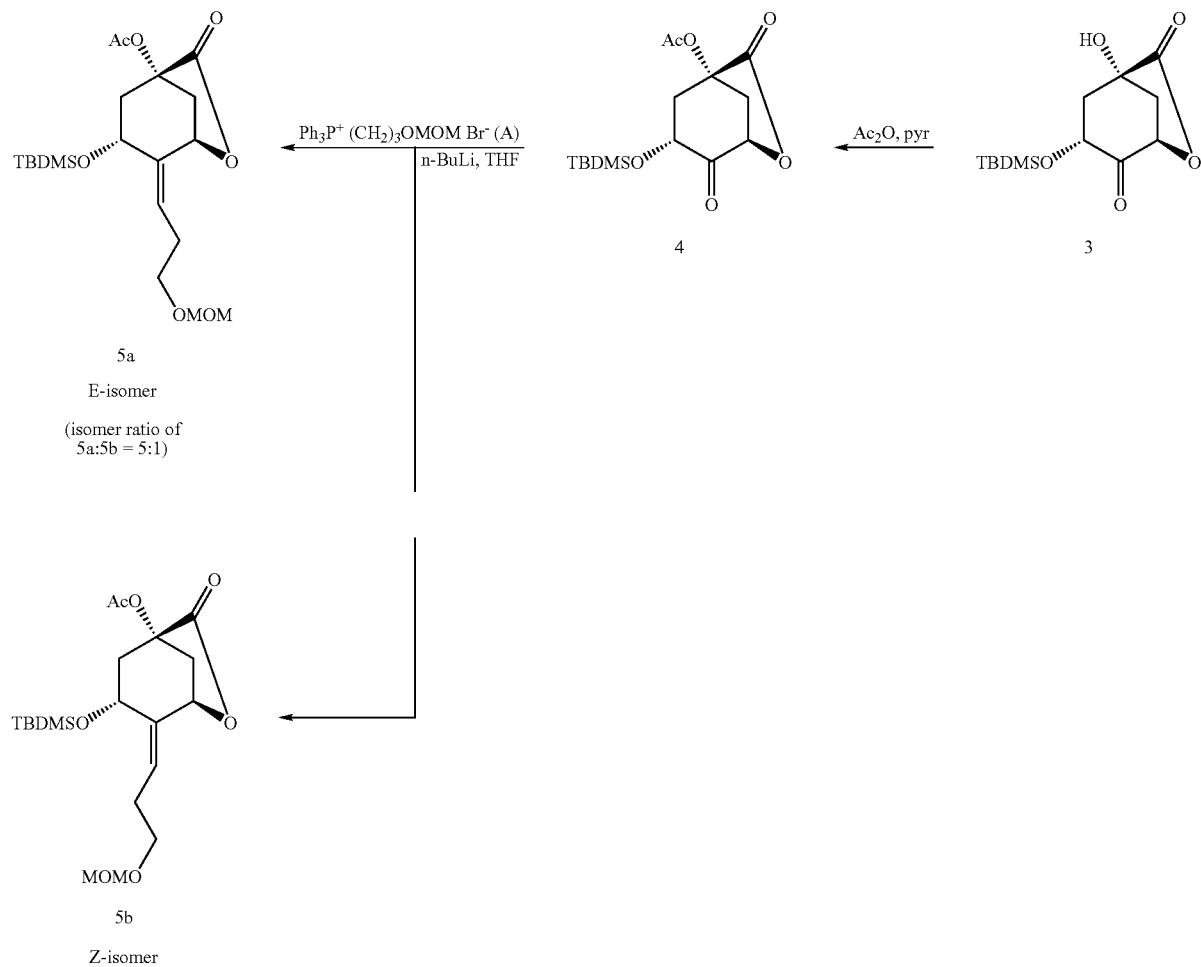
MOM = —CH₂OCH₃
TBDMS = —Si-t-BuMe₂
SCHEME II
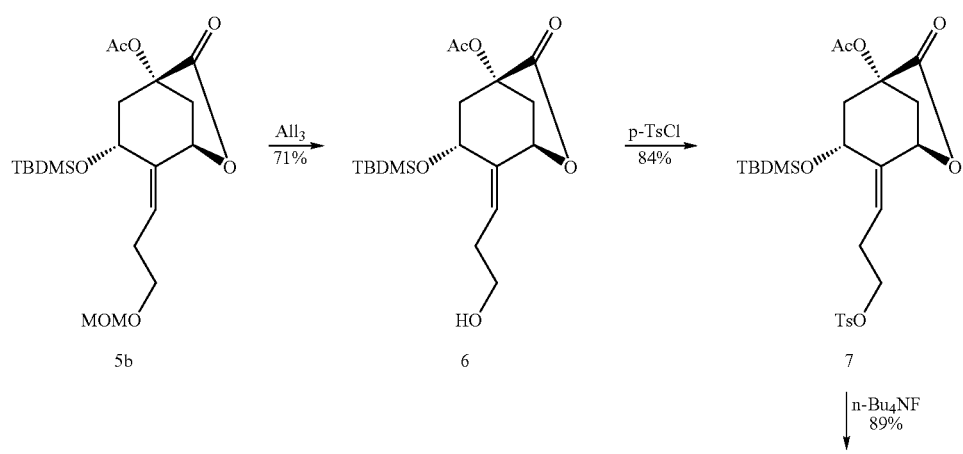

-continued
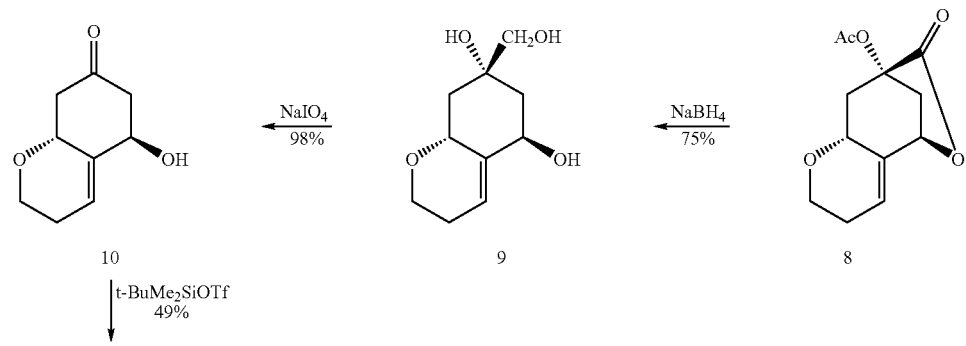
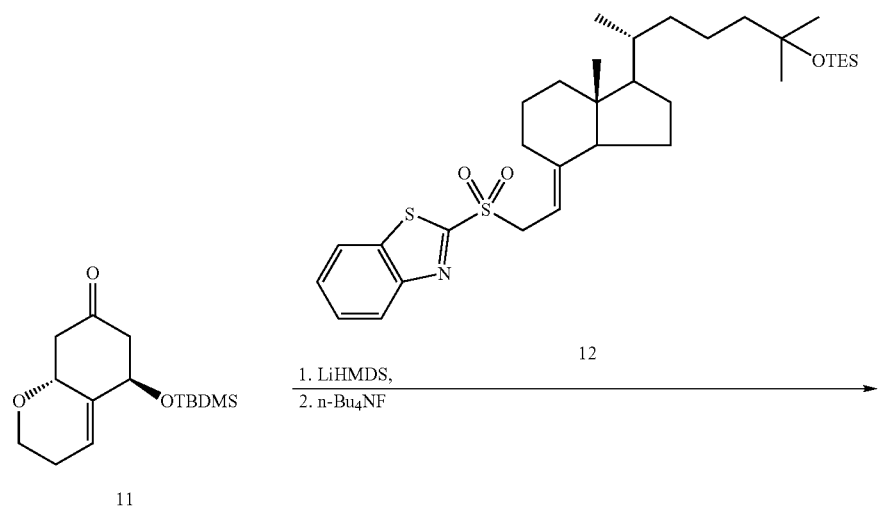
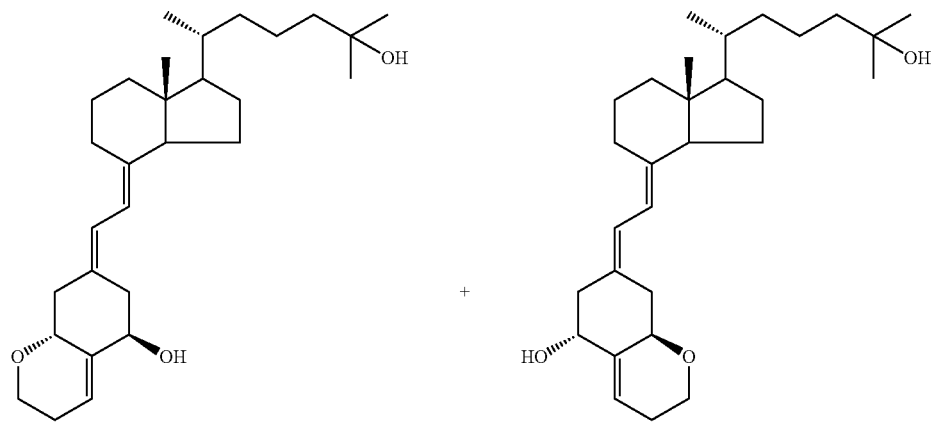

SCHEME III

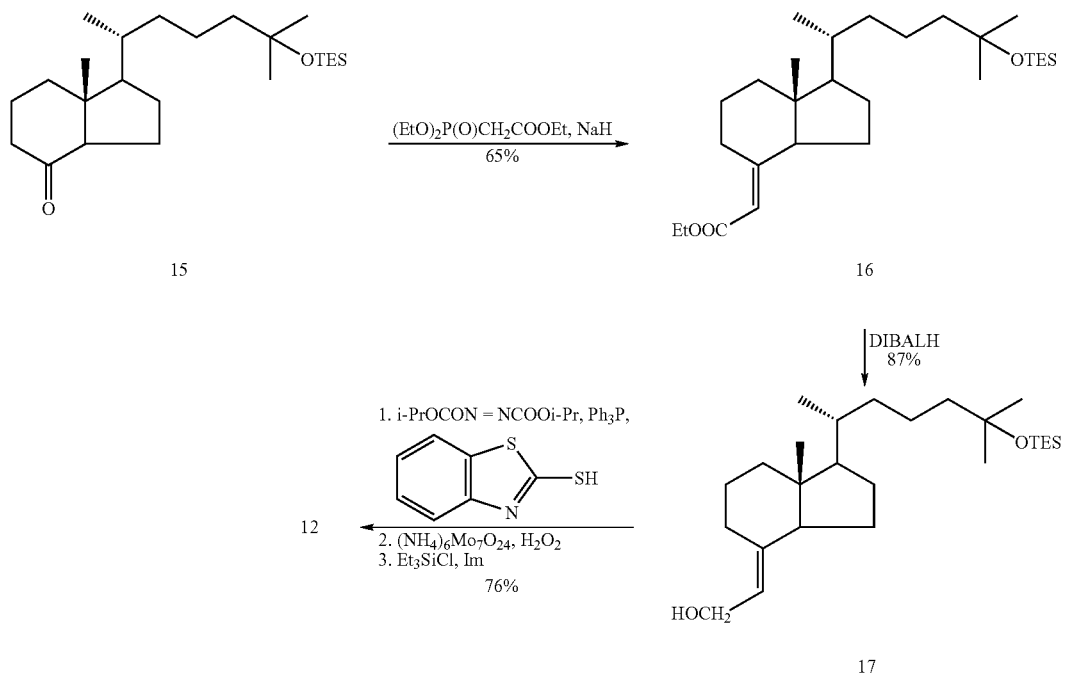

Biological Activity of 1α,25-Dihydroxy (Analog 13, REV-B) and 3β,25-Dihydroxy (Analog 14, REV-A) 19-NOR Vitamin $D_3$ Compounds The introduction of a heterocyclic ring connecting 3β-oxygen and carbon-2 (analog 13, REV-B) or 1α-oxygen and carbon-2 (analog 14, REV-A) markedly diminished binding to the full length recombinant rat vitamin D receptor, as compared to 1α,25-dihydroxyvitamin $D_3$. REV-B had little binding activity for VDR, while REV-A was 3 orders of magnitude less active than 1,25-$(OH)_2D_3$ (FIG. 1). Despite poor receptor binding activity in vitro, these compounds in vivo had significant activity on bone. Thus, REV-A and REV-B are highly selective analogs with unique biological activity.

Figure 4:
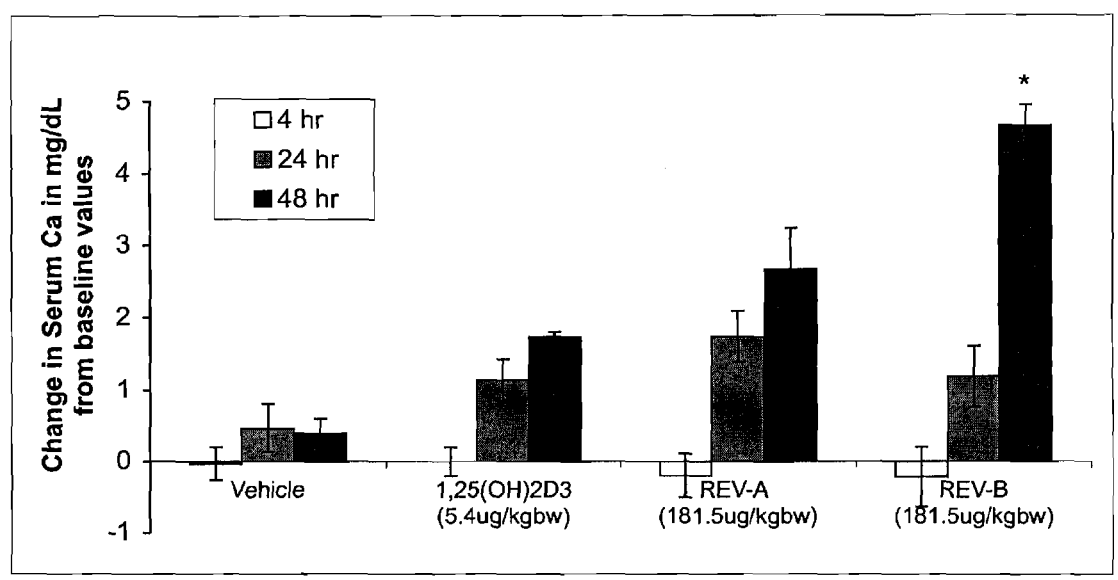

FIG. 4 demonstrates that REV-A and REV-B have considerable bone calcium mobilization activity, as compared to 1,25$(OH)_2D_3$, at the doses tested.

FIG. 4 thus illustrates that REV-A and REV-B may be characterized as having significant calcemic activity. Their preferential activity on bone calcium mobilizing activity allows the in vivo administration of these compounds for the treatment and prophylaxis of metabolic bone diseases. Because of their preferential activity on bone, these compounds would be preferred therapeutic agents for the treatment and prophylaxis of diseases such as osteoporosis, especially low bone turnover osteoporosis, steroid induced osteoporosis, senile osteoporosis or postmenopausal osteoporosis, as well as osteomalacia and renal osteodystrophy.

Figure 2:
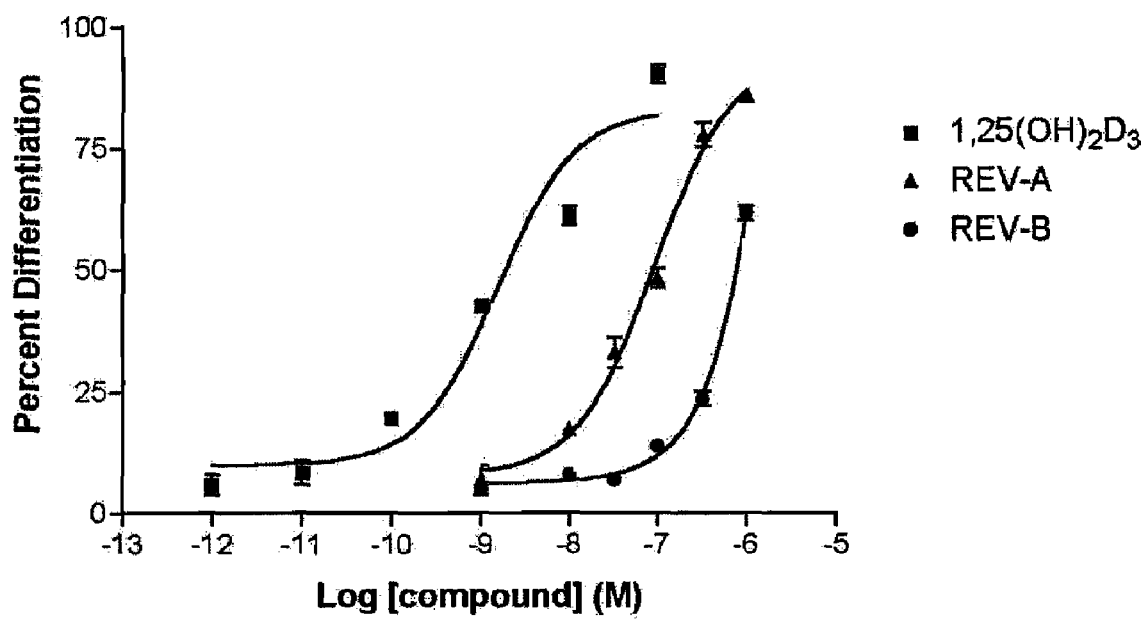
Figure 3:
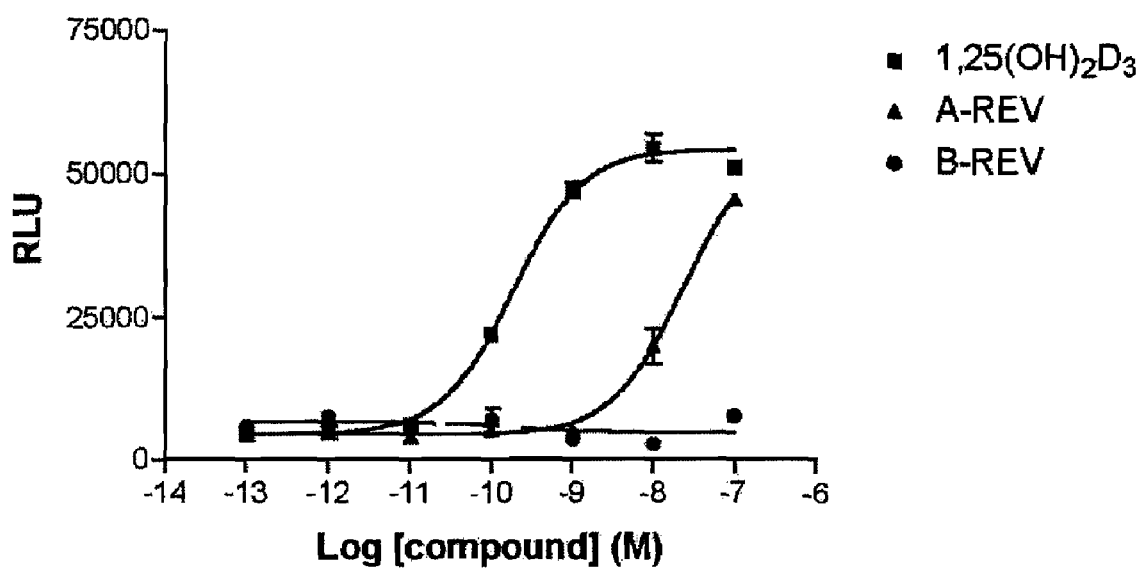

FIG. 2 illustrates that REV-A and REV-B are considerably less active than 1,25$(OH)_2D_3$ on HL-60 cell differentiation FIG. 3 illustrates that the compound REV-A has much less transcriptional activity than 1α,25-dihydroxyvitamin $D_3$ in bone cells, while compound REV-B is inactive in this assay. It seems possible that REV-A and REV-B may be converted in vivo to free acid forms that possess activity in bone.

The activity of REV-A and REV-B on HL-60 differentiation suggests they will be active in suppressing growth of parathyroid glands and in the suppression of the prepropar-athyroid gene. These analogs having relatively high calcemic activity are also expected to be useful as a therapy to treat hypoparathyroidism since they are effective to raise blood calcium levels.

Experimental Methods

The compounds of the invention were prepared and studied using the following methods.

Vitamin D Receptor Binding

Test Material

Protein Source

Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in $TEDK_{50}$ (50 mM Tris, 1.5 mM EDTA, pH7.4, 5 mM DTT, 150 mM KCl) with 0.1% Chaps detergent. The receptor protein and ligand concentration was optimized such that no more than 20% of the added radiolabeled ligand was bound to the receptor.

Study Drugs

Unlabeled ligands were dissolved in ethanol and the concentrations determined using UV spectrophotometry (1,25(OH)$_2$D$_3$: molar extinction coefficient=18,200 and $\lambda_{max}$=265 nm). Radiolabeled ligand ($^3$H-1,25(OH)$_2$D$_3$, ~159 Ci/mmole) was added in ethanol at a final concentration of 1 nM.

Assay Conditions

Radiolabeled and unlabeled ligands were added to 100 mcl of the diluted protein at a final ethanol concentration of $\leq$10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material

Study Drugs

The study drugs were dissolved in ethanol and the concentrations determined using UV spectrophotometry. Serial dilutions were prepared so that a range of drug concentrations could be tested without changing the final concentration of ethanol ($\leq$0.2%) present in the cell cultures.

Cells

Human promyelocytic leukemia (HL60) cells were grown in RPMI-1640 medium containing 10% fetal bovine serum. The cells were incubated at 37° C. in the presence of 5% $CO_2$.

Assay Conditions

HL60 cells were plated at $1.2 \times 10^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer. RLU=relative luciferase units Antagonism was tested by adding a combination of 1,25(OH)$_2$D$_3$ and the compound in the same well keeping the final ethanol concentration the same.

Bone Calcium Mobilization

1st In Vivo Study

Female, CD-1 mice (6 weeks old) were purchased from Harlan Sprague-Dawley. Upon arrival, the animals were placed in a room with filtered lighting and fed a purified, D-deficient diet (Suda et al 1970 J. Nutrition) for 17 weeks. After this time, the mice were assigned to 4 groups (n=3/group), and given a single, intraperitoneal injection of vehicle (5% ethanol:95% propylene glycol), 1,25(OH)$_2$D$_3$, REV-A or REV-B. Blood was collected prior to dose administration and multiple times thereafter. Serum calcium was measured by diluting with 0.1% lanthum chloride and reading the absorbance using an atomic absorption spectrometer. The change in serum calcium from pre-dose values (baseline) is reported.

2nd In Vivo Study 6-7 week old female CD-1 mice were purchased from Harlan (Indianapolis, Ind.). The animals were group housed and fed a purified diet containing 0.47% calcium. (Suda et al 1970 J. Nutrition). After a 5-7 day acclimation period, the animals were assigned to treatment groups (n=5-6/group) and given a single dose of the designated analogues by intraperitoneal injection. Blood was collected for serum calcium concentration analyses immediately prior to dose administration and 72 hours following dose delivery. Serum calcium were analyzed as described above.

3rd In Vivo Study 6-7 week old female CD-1 mice were purchased from Harlan (Indianapolis, Ind.). The animals were group housed and fed a purified diet containing 0.47% calcium. (Suda et al 1970 J. Nutrition). After a 5-7 day acclimation period, the animals were assigned to treatment groups (n=5/group) and given a single dose of the designated analogues by intraperitoneal injection or oral gavage. Blood was collected for serum calcium concentration analyses at various timepoints following dose delivery. Serum calcium was analyzed as described above.

Statistical Analysis

In vivo data were analyzed by one-way ANOVA followed by pairwise comparisons when significant overall differences were detected. Post-hoc analyses includes, Tukey's, Scheffe's, and Fisher's LSD tests. Only differences (p<0.05) that were present in two out of the three post-hoc tests were considered significant.

Interpretation of Data

VDR binding. HL60 cell differentiation, and transcription activity. REV-A ($K_i=3.0 \times 10^{-8}$M) and REV-B ($K_i=>10^{-5}$M) have much lower ability than the natural hormone 1$\alpha$,25-dihydroxyvitamin D$_3$ ($K_i=5.0 \times 10^{-11}$M) in their ability to compete with [$^3$H]-1,25(OH)$_2$D$_3$ for binding to the full-length recombinant rat vitamin D receptor (FIG. 1). Among the synthesized derivatives of 19-nor-1$\alpha$,25-(OH)$_2$D$_3$ REV-B and REV-A, possessing an additional dihydropyrane ring, only the latter has significant binding affinity to the vitamin D receptor albeit decreased more than five hundred times compared to 1,25(OH)$_2$D$_3$ (FIG. 1). REV-A (EC$_{50}$=1.0$\times$10$^{-7}$M) and REV-B (EC$_{50}$=1.0$\times$10$^{-6}$M) are also considerably lower in their ability to promote HL60 differentiation as compared to 1$\alpha$,25-dihydroxyvitamin D$_3$ (EC$_{50}$=2.0$\times$10$^{-9}$M) (See FIG. 2). Studies on the ability of the vitamins REV-B and REV-A to induce differentiation of human promyelocyte HL-60 cells into monocytes show that their potency is decreased by three and two orders of magnitude, respectively, in comparison with the natural hormone (FIG. 2). Also, compound REV-A (EC$_{50}$=3.0$\times$10$^{-8}$M) has much lower transcriptional activity in bone cells than 1$\alpha$,25-dihydroxyvitamin D$_3$ (EC$_{50}$=2.0$\times$10$^{-10}$M) while REV-B appears to have essentially no transcriptional activity. (See FIG. 3). Thus, REV-A has weak transcriptional activity, indicated in the 24-hydroxylase (CYP-24) promoter driving luciferase reporter gene system, whereas REV-B has been found completely inactive in this regard (FIG. 3).

Calcium mobilization from bone in vitamin D-deficient animals. Using vitamin D-deficient mice on a low calcium diet (0.02%), the activities of REV-A, REV-B and $1,25(OH)_2D_3$ in bone were tested. As expected, the native hormone ($1,25(OH)_2D_3$) increased serum calcium levels at the dosage tested (FIG. 4).

Figure 5:
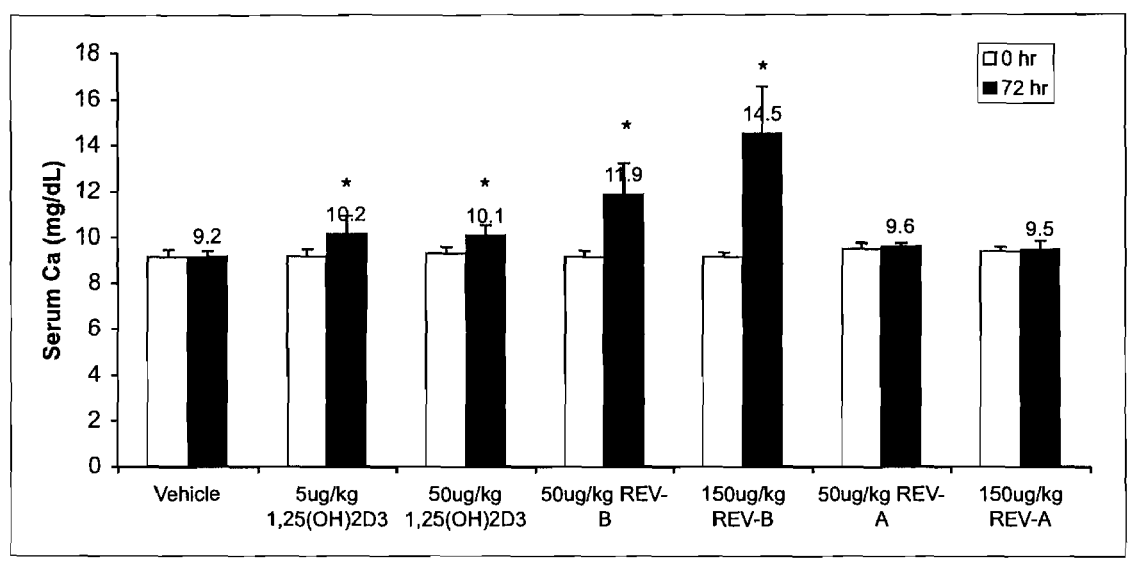
Figure 6:
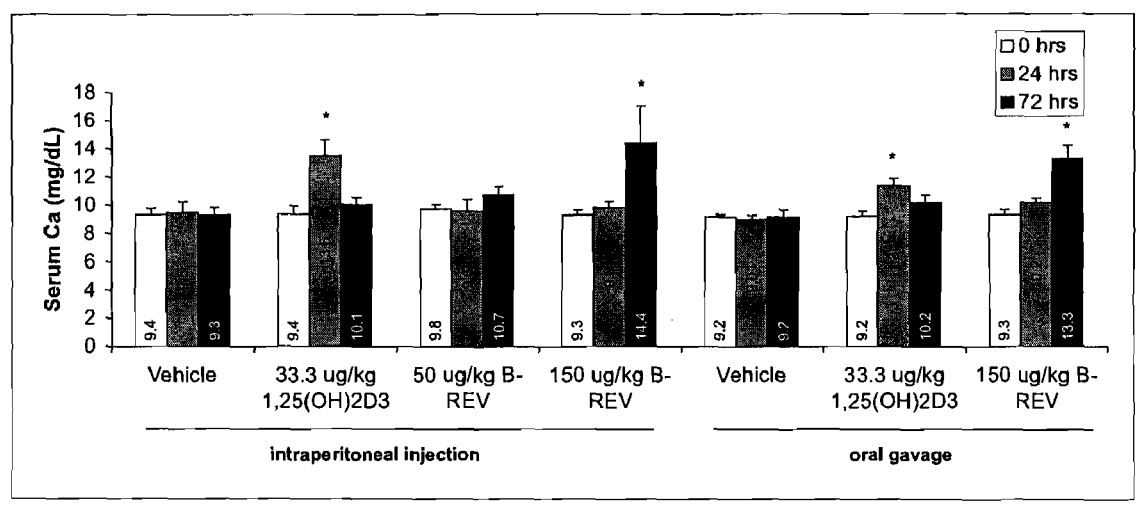

Taking into account the above described in vitro results, very low calcemic activity or even complete lack of in vivo activity might be expected for the synthesized analogs REV-B and REV-A. However, studies conducted with these compounds in vivo in D-deficient mice in doses exceeding thirty times that of the natural hormone, show that these compounds have a similar calcemic response after 24 h as calcitriol and isomer REV-B was markedly more active 48 hours after the dose was administered (FIG. 4). A second study conducted in D-sufficient CD-1 mice again showed the remarkable in vivo activity of REV-B to raise blood calcium levels (FIG. 5). However, no significant increase in serum calcium was detected with REV-A, which is consistent with the D-deficient mouse study in that the apparent increase in serum calcium after administration of REV-A did not turn out to be statistically significant given the variation and the few animals per group (n=3). Interestingly, the analog that had the least amount of activity in vitro (REV-B-α-chair form), has the most in vivo activity and furthermore, its potency in vivo is similar to that of the native hormone. The last experiment conducted with REV-B is shown in FIG. 6. This study was again performed in D-sufficient CD-1 mice. Two different routes of administration (oral gavage vs. intraperitoneal injection) were studied. Both routes of administration are effective at causing an increase in serum calcium; however, intraperitoneal injection is more effective than oral gavage. This observation is similar to that of the native hormone. It should also be noted that like in the D-deficient animals, there is a significant delay compared to $1,25(OH)_2D_3$ for an observed increase in serum calcium to occur when the animals are given REV-B. It can be suggested that in the living organism both analogs might undergo some metabolic changes, possible cleavage of dihydropyrane rings, resulting in one compound with no or very little biological activity and the other with pronounced in vivo activity that takes longer to manifest when compared to the native hormone. If ring cleavage is the metabolic conversion taking place, it is not hard to understand why REV-B is much more active than REV-A in vivo compared to the in vitro situation as REV-A would not have a 1-hydroxy group which is known to be very important for VDR binding. Further studies are required to prove that ring opening is the explanation for the disparate results obtained in vivo versus in vitro.

Discussion

Conformational equilibrium of the cyclohexane ring A of vitamin D compounds and its influence on biological activity has been studied for more than three decades. In 1974, Okamura hypothesized that the β-chair form—, which possesses an equatorial 1α-hydroxyl, is responsible for the biological activities of vitamin D analogs. Our early studies on 1α,25-dihydroxy-10,19-dihydrovitamin $D_3$ seemed to contradict this suggestion. Then, the results of biological testing and conformational analysis of 2-methyl substituted analogs of the hormone, synthesized by Japanese scientists, and their 19-nor-counterparts obtained in our laboratory, prompted us to suggest that an axial orientation of 1α-OH might be of crucial importance for exertion of calcemic activity. It was found that 2α-alkylated vitamins, characterized by strong bias (above 90%) toward conformers with the axial hydroxyl at C-1, are much more biologically potent then the respective 2p3-isomers existing in solution primarily in the opposite β-chair form. Afterward, however, the Moras group reported the crystal structure of the hVDR ligand binding domain (LBD) complexed with calcitriol and several other ligands characterized by an unnatural configuration at C-20. All these results clearly indicated that the receptor binds (at least in the crystalline state) vitamin D compounds having their A-rings in the β-chair conformation. Even more convincing was the recent report from our laboratory, in which Vanhooke described the crystal structure of the rat VDR LBD complexed with a 2α-methyl-substituted vitamin $D_3$ analog, possessing highly elevated biopotency in both intestine and bone. The study shows that this vitamin D compound also adopts the β-chair A-ring conformation in its crystalline complex with VDR. However, in all these cases, interconversion between the ligand's A-ring chair conformers was not prohibited, and therefore, some doubts could arise which form of the ligand-VDR complex actually exists in the real physiological environment. Thus, it was tempting to synthesize and biologically evaluate a vitamin D compound possessing an axially oriented hydroxyl group at C-1 and unable to change its A-ring conformation. The 1α,25-dihydroxyvitamin $D_3$ analog REV-B, described in the present work, fulfills these requirements. It was established that such vitamin D does not bind to the VDR and lacks activity in cellular differentiation and in inducing transcription of a vitamin D-responsive gene. Notably, its isomer REV-A possessing free 3β- and 25-hydroxyl groups, but characterized by a "frozen" A-ring β-chair conformation, was found to be ca. 560 times less potent in binding to the receptor than the hormone. Such binding ability could be expected for a 25-OH-$D_3$ derivative in which the 1α-oxygen function cannot act as a hydrogen donor and create the hydrogen bonds with the amino acids from the LBD. The biological results obtained in vitro on the synthesized analogs REV-B and REV-A clearly confirm that the A-ring β-chair conformation and, consequently, equatorial orientation for the 1α-OH is necessary for the vitamin D compound to ensure its binding with VDR and exertion of biological activity. Biological evaluation of the test vitamins in vivo does not generate results consistent with those obtained in vitro, most likely due to metabolic transformation of both compounds occurring in the living organisms.

Conclusions

The conformations of the A-rings of vitamins REV-B and REV-A, as well as the structures of intermediate compounds used for the construction of their A-ring parts, were established by NMR spectroscopic methods. Analysis of the observed vicinal proton coupling constants proved that in the synthesized vitamin D analogs REV-B and REV-A, possessing an additional dihydropyrane ring, their A-rings could only exist in a single confirmation, α- and β-chair, respectively. Biological in vitro testing of the analogs REV-B and REV-A allowed us to conclude that the presence of an equatorially oriented free hydroxyl at C-1 is necessary for binding to the vitamin D receptor. Thus, only the vitamin D that can assume a β-chair A-ring conformation can be accepted by the VDR further inducing conformational changes crucial for the ligand-receptor activation.

These results illustrate that REV-A and REV-B are excellent candidates for numerous human therapies as described herein, and that they may be particularly useful in a number of circumstances such as suppression of secondary hyperparathyroidism of renal osteodystrophy. The fact that REV-A and REV-B in vivo have impressive activity on bone suggests that they would be useful in treating metabolic bone diseases, especially renal osteodystrophy, osteoporosis, osteopenia, vitamin D-resistant rickets, and osteomalacia.

The compounds of the invention of formula I and II are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I and/or II. Administration of the compound or the pharmaceutical compositions to the subject inhibits adipocyte differentiation, inhibits gene transcription, and/or reduces body fat in the animal subject. The animal may be a human, a domestic animal such as a dog or a cat, or an agricultural animal, especially those that provide meat for human consumption, such as fowl like chickens, turkeys, pheasant or quail, as well as bovine, ovine, caprine, or porcine animals.

For prevention and/or treatment purposes, the compounds of this invention defined by formula I and II may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and II may be administered orally, topically, parenterally, rectally, nasally, sublingually, or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 µg to 10 mg per day of the compounds I or II, preferably from about 0.1 µg to about 1 mg per day, is appropriate for prevention and/or treatment purposes, such dose being adjusted according to the disease to be treated, its severity and the response of the subject as is well understood in the art. Since the compounds exhibit specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatments comprise an effective amount of the compounds I or II as defined by the above formula I and II as the active ingredient, and a suitable carrier. An effective amount of such compound for use in accordance with this invention is from about 0.01 µg to about 10 mg per gm of composition, preferably from about 0.1 µg to about 1 mg per gram of composition, and may be administered topically, transdermally, orally, rectally, nasally, sublingually or parenterally in dosages of from about 0.01 µg/day to about 10 mg/day, and preferably from about 0.1 µg/day to about 1 mg/day.

The compounds I and II may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I and II may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100µ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

What is claimed is:

1. A compound having the formula:

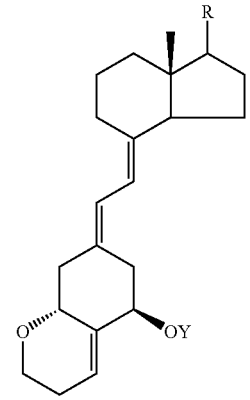

where Y is selected from the group consisting of hydrogen and a hydroxy-protecting group, and where the group R represents an alkyl, hydrogen, hydroxyalkyl, or fluoroalkyl group, or R may represent a side chain of the formula:

where Z in the above side chain structure is selected from Y, —OY, —$CH_2$OY, —C≡CY and —CH═CHY, where the double bond in the side chain may have the cis or trans geometry, and where Y is selected from hydrogen, methyl, —COR⁵ and a radical of the structure:

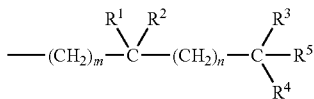

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group having a general formula $C_kH_{2k}$— where k is an integer, the group $=CR^2R^3$, or the group —$(CH_2)_p$—, where p is an integer from 2 to 5, and where $R^3$ and $R^4$, taken together, represent an oxo group, or the group —$(CH_2)_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —CH(CH₃)—, —(CH₂)ₘ—, —CR₁R₂— or —(CH₂)ₙ— at positions 20, 22, and 23, respectively, may be replaced by an oxygen or sulfur atom.

2. The compound of claim 1 wherein Y is hydrogen.

3. A pharmaceutical composition containing an effective amount of at least one compound as claimed in claim 1 together with a pharmaceutically acceptable excipient.

4. The pharmaceutical composition of claim 3 wherein said effective amount comprises from about 0.01 µg to about 10 mg per gram of composition.

5. The pharmaceutical composition of claim 3 wherein said effective amount comprises from about 0.1 µg to about 1 mg per gram of composition.

6. A method of treating a metabolic bone disease comprising administering to a subject with said disease an effective amount of a compound having the formula:

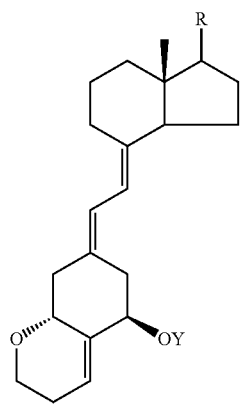

where Y is selected from the group consisting of hydrogen and a hydroxy-protecting group, and where the group R represents an alkyl hydrogen, hydroxyalkyl, or fluoroalkyl group, or R may represent a side chain of the formula:

where Z in the above side chain structure is selected from Y, —OY, —CH₂OY, —C≡CY and —CH=CHY, where the double bond in the side chain may have the cis or trans geometry, and where Y is selected from hydrogen, methyl, —COR⁵ and a radical of the structure:

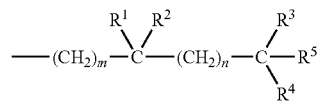

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group having a general formula $C_kH_{2k}$— where k is an integer, the group $=CR^2R^3$, or the group —$(CH_2)_p$—, where p is an integer from 2 to 5, and where $R^3$ and $R^4$, taken together, represent an oxo group, or the group —$(CH_2)_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —CH(CH₃)—, —(CH₂)ₘ—, —CR₁R₂— or —(CH₂)ₙ— at positions 20, 22, and 23, respectively, may be replaced by an oxygen or sulfur atom.

7. The method of claim 6 where the disease is senile osteoporosis.

8. The method of claim 6 where the disease is postmenopausal osteoporosis.

9. The method of claim 6 where the disease is steroid-induced osteoporosis.

10. The method of claim 6 where the disease is low bone turnover osteoporosis.

11. The method of claim 6 where the disease is osteomalacia.

12. The method of claim 6 wherein the compound is administered orally.

13. The method of claim 6 wherein the compound is administered parenterally.

14. The method of claim 6 wherein the compound is administered transdermally.

15. The method of claim 6 wherein the compound is administered rectally.

16. The method of claim 6 wherein the compound is administered nasally.

17. The method of claim 6 wherein the compound is administered sublingually.

18. The method of claim 6 wherein the compound is administered in a dosage of from about 0.01 µg/day to about 10 mg/day.

19. The method of claim 6 wherein the compound is a 1α,25-dihydroxy-19-norvitamin D₃ compounds having the formula:

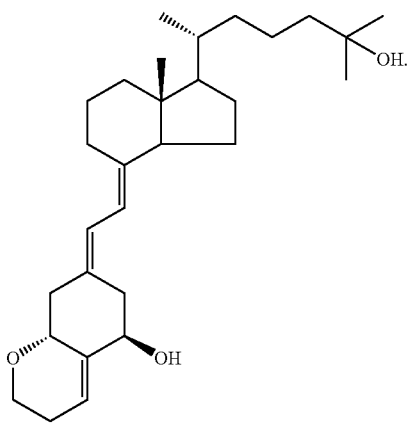

20. A method of treating osteopenia comprising administering to a subject with osteopenia an effective amount of a compound having the formula:

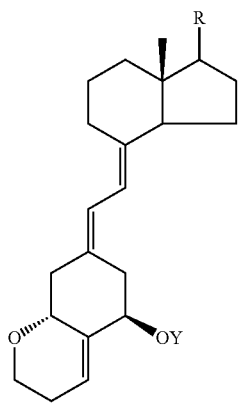

where Y is selected from the group consisting of hydrogen and a hydroxy-protecting group, and where the group R represents an alkyl, hydrogen, hydroxyalkyl, or fluoroalkyl group, or R may represent a side chain of the formula:

where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^5$ and a radical of the structure:

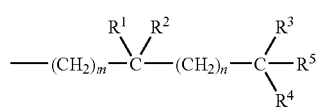

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group ═CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

21. The method of claim 20 wherein the compound is administered orally.

22. The method of claim 20 wherein the compound is administered parenterally.

23. The method of claim 20 wherein the compound is administered transdermally.

24. The method of claim 20 wherein the compound is administered rectally.

25. The method of claim 20 wherein the compound is administered nasally.

26. The method of claim 20 wherein the compound is administered sublingually.

27. The method of claim 20 wherein the compound is administered in a dosage of from about 0.01 μg/day to about 10 mg/day.

28. The method of claim 6 wherein the compound is a 1α,25-dihydroxy-19-norvitamin D$_3$ compounds having the formula:

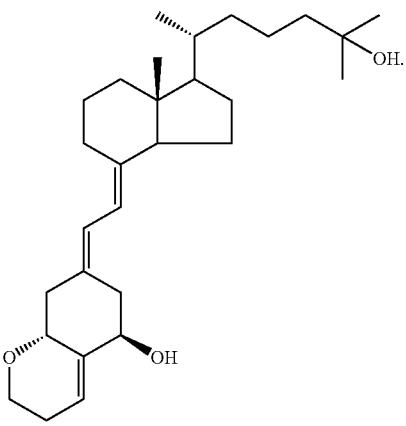

29. A method of treating renal osteodystrophy comprising administering to a subject with renal osteodystrophy an effective amount of a compound having the formula:

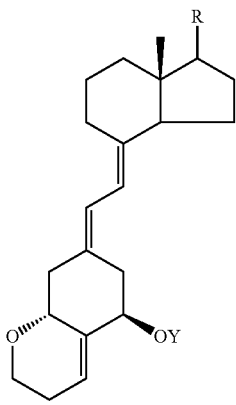

where Y is selected from the group consisting of hydrogen and a hydroxy-protecting group, and where the group R represents an alkyl, hydrogen, hydroxyalkyl, or fluoroalkyl group, or R may represent a side chain of the formula:

where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^5$ and a radical of the structure:

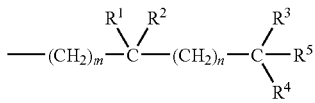

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group ═CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

30. The method of claim 29 wherein the compound is administered orally.

31. The method of claim 29 wherein the compound is administered parenterally.

32. The method of claim 29 wherein the compound is administered transdermally.

33. The method of claim 29 wherein the compound is administered rectally.

34. The method of claim 29 wherein the compound is administered nasally.

35. The method of claim 29 wherein the compound is administered sublingually.

36. The method of claim 29 wherein the compound is administered in a dosage of from about 0.01 μg/day to about 10 mg/day.

37. The method of claim 29 wherein the compound is a 1α,25-dihydroxy-19-norvitamin D$_3$ compounds having the formula:

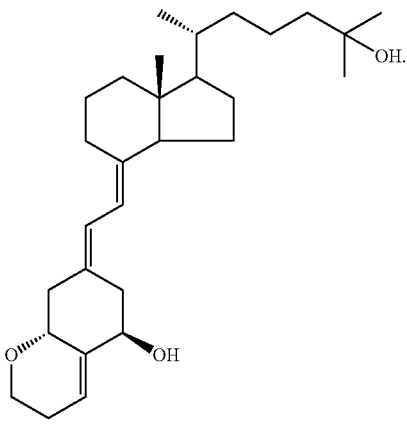

38. A compound having the formula:

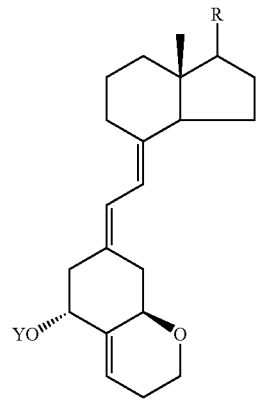

where Y is selected from the group consisting of hydrogen and a hydroxy-protecting group, and where the group R represents an alkyl, hydrogen, hydroxyalkyl, or fluoroalkyl group, or R may represent a side chain of the formula:

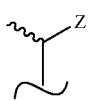

where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR⁵ and a radical of the structure:

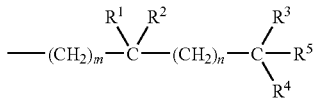

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group having a general formula $C_kH_{2k}$— where k is an integer, the group $=CR^2R^3$, or the group —$(CH_2)_p$—, where p is an integer from 2 to 5, and where $R^3$ and $R^4$, taken together, represent an oxo group, or the group —$(CH_2)_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —CH(CH₃)—, —(CH₂)$_m$—, —CR₁R₂— or —(CH₂)$_n$— at positions 20, 22, and 23, respectively, may be replaced by an oxygen or sulfur atom.

39. The compound of claim 38 wherein Y is hydrogen.

40. A pharmaceutical composition containing an effective amount of at least one compound as claimed in claim 38 together with a pharmaceutically acceptable excipient.

41. The pharmaceutical composition of claim 40 wherein said effective amount comprises from about 0.01 μg to about 10 mg per gram of composition.

42. The pharmaceutical composition of claim 40 wherein said effective amount comprises from about 0.1 μg to about 1 mg per gram of composition.

43. A method of treating a metabolic bone disease comprising administering to a subject with said disease an effective amount of a compound having the formula:

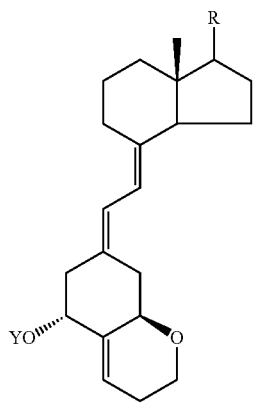

where Y is selected from the group consisting of hydrogen and a hydroxy-protecting group, and where the group R represents an alkyl, hydrogen, hydroxyalkyl, or fluoroalkyl group, or R may represent a side chain of the formula:

where Z in the above side chain structure is selected from Y, —OY, —CH₂OY, —C≡CY and —CH=CHY, where the double bond in the side chain may have the cis or trans geometry, and where Y is selected from hydrogen, methyl, —COR⁵ and a radical of the structure:

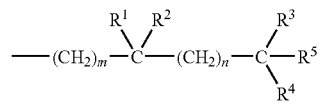

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group having a general formula $C_kH_{2k}$— where k is an integer, the group $=CR^2R^3$, or the group —$(CH_2)_p$—, where p is an integer from 2 to 5, and where $R^3$ and $R^4$, taken together, represent an oxo group, or the group —$(CH_2)_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —CH(CH₃)—, —(CH₂)$_m$—, —CR₁R₂— or —(CH₂)$_n$— at positions 20, 22, and 23, respectively, may be replaced by an oxygen or sulfur atom.

44. The method of claim 43 where the disease is senile osteoporosis.

45. The method of claim 43 where the disease is postmenopausal osteoporosis.

46. The method of claim 43 where the disease is steroid-induced osteoporosis.

47. The method of claim 43 where the disease is low bone turnover osteoporosis.

48. The method of claim 43 wherein the disease is osteomalacia.

49. The method of claim 43 wherein the compound is administered orally.

50. The method of claim 43 wherein the compound is administered parenterally.

51. The method of claim 43 wherein the compound is administered transdermally.

52. The method of claim 43 wherein the compound is administered rectally.

53. The method of claim 43 wherein the compound is administered nasally.

54. The method of claim 43 wherein the compound is administered sublingually.

55. The method of claim 43 wherein the compound is administered in a dosage of from about 0.01 μg/day to about 10 mg/day.

56. The method of claim 43 wherein the compound is a 3β,25-dihydroxy-19-norvitamin D₃ compounds having the formula:

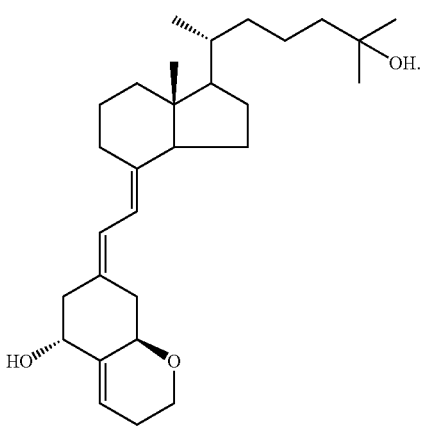

57. A method of treating osteopenia comprising administering to a subject with osteopenia an effective amount of a compound having the formula:

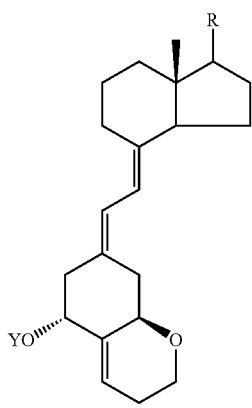

where Y is selected from the group consisting of hydrogen and a hydroxy-protecting group, and where the group R represents an alkyl, hydrogen, hydroxyalkyl, or fluoroalkyl group, or R may represent a side chain of the formula:

where Z in the above side chain structure is selected from Y, —OY, —CH$_2$OY, —C≡CY and —CH=CHY, where the double bond in the side chain may have the cis or trans geometry, and where Y is selected from hydrogen, methyl, —COR$^5$ and a radical of the structure:

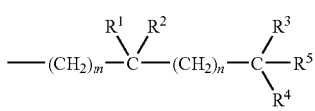

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group =CR$^2$R$^3$, or the group —(CH$_2$)$_p$—, where p is an integer from 2 to 5, and where R$^3$ and R$^4$, taken together, represent an oxo group, or the group —(CH$_2$)$_q$— where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

58. The method of claim 57 wherein the compound is administered orally.

59. The method of claim 57 wherein the compound is administered parenterally.

60. The method of claim 57 wherein the compound is administered transdermally.

61. The method of claim 57 wherein the compound is administered rectally.

62. The method of claim 57 wherein the compound is administered nasally.

63. The method of claim 57 wherein the compound is administered sublingually.

64. The method of claim 57 wherein the compound is administered in a dosage of from about 0.01 μg/day to about 10 mg/day.

65. The method of claim 57 wherein the compound is a 3β,25-dihydroxy-19-norvitamin D$_3$ analog having the formula:

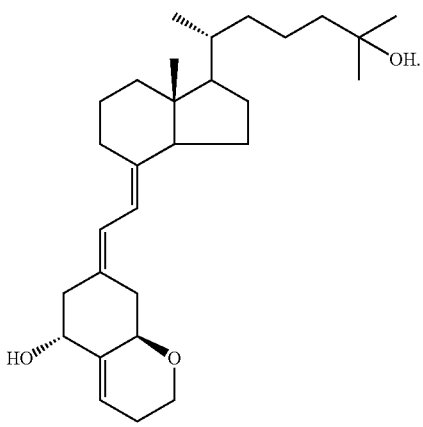

66. A method of treating renal osteodystrophy comprising administering to a subject with renal osteodystrophy an effective amount of a compound having the formula:

39

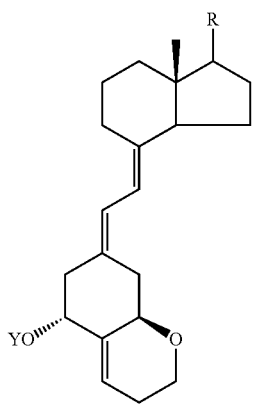

where Y is selected from the group consisting of hydrogen and a hydroxy-protecting group, and where the group R represents an alkyl, hydrogen, hydroxyalkyl, or fluoroalkyl group, or R may represent a side chain of the formula:

where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^5$ and a radical of the structure:

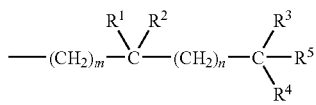

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group ═CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

67. The method of claim 66 wherein the compound is administered orally.

68. The method of claim 66 wherein the compound is administered parenterally.

69. The method of claim 66 wherein the compound is administered transdermally.

70. The method of claim 66 wherein the compound is administered rectally.

71. The method of claim 66 wherein the compound is administered nasally.

72. The method of claim 66 wherein the compound is administered sublingually.

73. The method of claim 66 wherein the compound is administered in a dosage of from about 0.01 µg/day to about 10 mg/day.

74. The method of claim 66 wherein the compound is a 3β,25-dihydroxy-19-norvitamin D$_3$ comoounds having the formula:

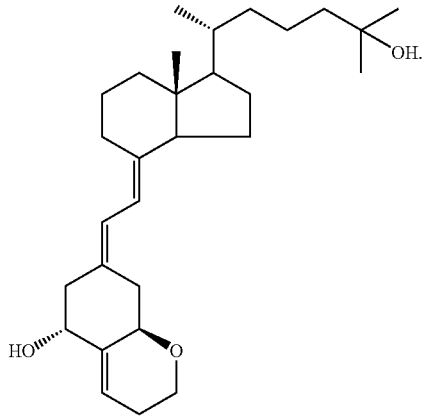

75. A compound having the formula:

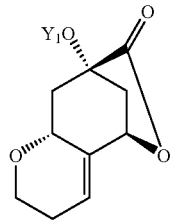

where Y$_1$ is selected from the group consisting of hydrogen and a hydroxy-protecting group.

76. The compound of claim 75 wherein Y$_1$ is an acyl group.

77. A compound having the formula:

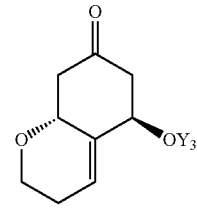

where Y$_3$ is selected from the group consisting of hydrogen and a hydroxy-protecting group.

78. The compound of claim 77 wherein Y$_3$ is hydrogen.

79. The compound of claim 77 wherein Y$_3$ is t-butyldimethylsilyl.

80. A compound having the formula:

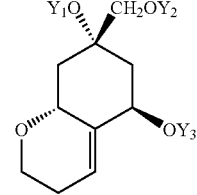

where Y$_1$, Y$_2$, and Y$_3$, which may be the same or different, are each selected from the group consisting of hydrogen and a hydroxy-protecting group.

81. The compound of claim 80 wherein Y$_1$, Y$_2$, and Y$_3$ are each hydrogen.

* * * * *